US008604077B2

(12) United States Patent
Wicks et al.

(10) Patent No.: US 8,604,077 B2
(45) Date of Patent: Dec. 10, 2013

(54) KETAL COMPOUNDS FROM POLYOLS AND OXOCARBOXYLATES

(75) Inventors: Douglas Alan Wicks, Plymouth, MN (US); Charles Todd Williams, Pittsburgh, PA (US); Sergey A. Selifonov, Plymouth, MN (US)

(73) Assignee: Segetis, Inc., Golden Valley, MN (US)

( * ) Notice: Subject to any disclaimer, the term of this patent is extended or adjusted under 35 U.S.C. 154(b) by 389 days.

(21) Appl. No.: 12/674,322

(22) PCT Filed: Sep. 4, 2008

(86) PCT No.: PCT/US2008/075225
§ 371 (c)(1),
(2), (4) Date: Jul. 29, 2011

(87) PCT Pub. No.: WO2009/032905
PCT Pub. Date: Mar. 12, 2009

(65) Prior Publication Data
US 2011/0319586 A1 Dec. 29, 2011

Related U.S. Application Data

(60) Provisional application No. 60/935,839, filed on Sep. 4, 2007, provisional application No. 60/935,843, filed on Sep. 4, 2007, provisional application No. 60/935,838, filed on Sep. 4, 2007, provisional application No. 60/935,877, filed on Sep. 5, 2007, provisional application No. 60/935,882, filed on Sep. 5, 2007, provisional application No. 60/935,881, filed on Sep. 5, 2007, provisional application No. 60/935,880, filed on Sep. 5, 2007, provisional application No. 60/935,875, filed on Sep. 5, 2007, provisional application No. 60/960,627, filed on Oct. 9, 2007.

(51) Int. Cl.
*A61K 31/36* (2006.01)
*C07D 407/12* (2006.01)

(52) U.S. Cl.
USPC .......................................... 514/452; 549/370

(58) Field of Classification Search
USPC .......................................... 514/452; 549/370
See application file for complete search history.

(56) References Cited

U.S. PATENT DOCUMENTS

| | | | |
|---|---|---|---|
| 2,004,115 A | 6/1935 | Izard | |
| 2,260,261 A | 1/1940 | Morey | |
| 2,556,135 A | 6/1951 | Croxall et al. | |
| 2,838,467 A | 6/1958 | Dobay | |
| 2,985,536 A | 5/1961 | Stein et al. | |
| 3,201,420 A | 8/1965 | Fuzesi et al. | |
| 3,963,800 A | 6/1976 | Gipp et al. | |
| 4,085,081 A | 4/1978 | Heckles et al. | |
| 4,792,411 A | 12/1988 | Walsh | |
| 5,095,098 A | 3/1992 | McLain et al. | |
| 5,202,413 A | 4/1993 | Spinu | |
| 5,552,513 A | 9/1996 | Bhatia | |
| 5,565,545 A | 10/1996 | Kriesche et al. | |
| 5,741,882 A | 4/1998 | Fujii et al. | |
| 5,917,059 A | 6/1999 | Bruchmann et al. | |
| 6,528,025 B1 | 3/2003 | Boesch et al. | |
| 6,806,392 B2 | 10/2004 | Boesch et al. | |
| 2003/0167681 A1 | 9/2003 | Delgado Puche | |
| 2004/0024260 A1 | 2/2004 | Winkler et al. | |
| 2006/0069230 A1 | 3/2006 | Papisov | |
| 2008/0242721 A1 | 10/2008 | Selifonov | |
| 2010/0048940 A1 | 2/2010 | Tulchinsky et al. | |
| 2010/0216915 A1 | 8/2010 | Bloom | |
| 2011/0021658 A1 | 1/2011 | Selifonov | |

FOREIGN PATENT DOCUMENTS

| | | |
|---|---|---|
| FR | 1445013 | 7/1966 |
| JP | 2002348451 A | 12/2002 |
| WO | 2005097723 A2 | 10/2005 |
| WO | 2007062118 A2 | 5/2007 |

OTHER PUBLICATIONS

Bechtold, et al., "Perfectly Alternating Copolymer of Lactic Acid and Ethylene Oxide as a Plasticizing Agent for Polylactide," Macromolecules 34: 8641-8648 (2001).

Burch, et al., "Synthesis of Cyclic Oligoesters and Their Rapid Polymerization to High Molecular Weight," Macromolecules 33: 5053-5064 (2000).

Carey, Francis A. and Sundberg, Richard J., Advanced Organic Chemistry, Second Edition, Part B: Reactions and Synthesis Plenum Press, NY (1983) p. 539-552.

Chopade, et al., "Acetalization of ethylene glycol with formaldehyde using cation-exchange resins as catalysts: batch versus reactive distillation," Reactive and Functional Polymers 34: 37-45 (1997).

Clarkson, et al., "Continuous Reactor Technology for Ketal Formation: An Improved Synthesis of Solketal," Organic Process Research & Development 5: 630-635 (2001).

Clerici, Angelo, et al., "Efficient Acetalisation of Aldehydes Catalyzed by Titanium Tetrachloride in a Basic Medium", Tetrahedron 54 (1998) p. 15679-15690.

Deutsch, et al., Investigations on heterogeneously catalysed condensations of glycerol to cyclic acetals, Journal of Catalysis 245: 428-435 (2007).

Gasparrini, F., "Synthesis of Dimethyl Acetals, Diethyl Acetals, and Cyclic Acetals Catalyzed by Aminopropylated Silica Gel Hydrocholoride(APSG-HCL)", Tetrahedron 40(9), (1984) p. 1491-1500.

Grajkowski, Andrzej et al., "Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group", J. Org. Chem, 2007, vol. 72, No. 3, 805-815.

(Continued)

*Primary Examiner* — Taofiq A Solola
(74) *Attorney, Agent, or Firm* — Cantor Colburn LLP

(57) ABSTRACT

Novel ketal compounds can be made from an oxocarboxylate and a triol. Novel polymeric structures are, in turn, synthesized from the ketal compounds. Such ketal compounds and associated polymers are useful in a broad range of applications as a substitute for materials derived from petroleum or other such nonrenewable resources.

46 Claims, No Drawings

(56) References Cited

OTHER PUBLICATIONS

Hiltunen, et al., Synthesis and Characterization of Lactic Acid Based Telechelic Prepolymers, Macromolecules 29: 8677-8682 (1996).

Hoydonckx, et al., "Esterification and transesterification of renewable chemicals," Topics in Catalysis 27(1-4): 83-96 (2004).

Imwinkelried, et al., "Diisopropyl (2S,3S)-2,3-0-Isopropylidenetartrate [1,3-Dioxolane-4,5-dicarboxylic acid, 2,2-dimethyl-, bis(1-methylethyl)ester, (4R-trans)-]," Organic Syntheses 8: 201-230 (1993).

International Search Report for PCT/US2008/075225, mailed Feb. 6, 2009, 2 pages.

International Preliminary Report on Patentability for PCT/US2008/07225 mailed Mar. 9, 2010, 6 pages.

International Preliminary Report on Patentability for PCT/US2008/079337, mailed Apr. 13, 2010, 9 pages.

Written Opinion of the International Searching Authority for PCT/US2008/075225, mailed Feb. 6, 2009, 5 pages.

Written Opinion of the International Searching Authority for PCT/US2008/079337, mailed Apr. 21, 2009, 8 pages.

Kim, et al., "Preparation of High-Molecular-Weight Poly(L-lactic acid)-Based Polymers Through Direct Condensation Polymerization in Bulk State," Journal of Applied Polymer Science 100: 466-472 (2006).

Li, Tong-Shuang, et al., "Montmorillonite Clay Catalysis. Part 2. An Efficient and Convenient Procedure for the Preparation of Acetals Catalysed by Montmorillonite K-10," J. Chem Research (S) 26-27 (1997).

Meher, et al., "Technical aspects of biodiesel production by transesterification—a review," RSER 194: 1-21 (2004).

Meskens, Frans A. J., Methods for the Preparation of Acetals from Alcohols or Oxiranes and Carbonyl Compounds, Synthesisn (1981) 501-522.

Nagahata, et al., "Solid-Phase Thermal Polymerization of Macrocyclic Ethylene Terephthalate Dimer Using Various Transesterification Catalysts," Journal of Polyer Science: Part A: Polymer Chemistry 38: 3360-3368 (2000).

Nagata, et al., "Synthesis and Applications of [2-Methyl-2(oxoalkyl)-1,3-dioxolan-4-yl] methyl Acrylates for Photocrosslinking Agent," Osaka Kogyo Gijutsu Shikensho Kiho 37(1): 8-16 (1986).

Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).

Newman, et al.," Kinetic and Equilibrium Studies of Cyclic Ketal Formation and Hydrolysis," The Journal of the American Oil Chemist's Society 80: 6350-6355 (1958).

Otera, Junzo, Esterificaton, Methods, Reactions, and Applications, Wiley-VCH Verlag GmbH & Co., (2003) p. 1-19.

Pang, et al., "Review of conventional and novel polymerization processes for polyesters," Prog. Polym. Sci. 31: 1009-1037 (2006).

Pasto, D. J. and Serve, M. P., "Neighboring Group Participation by Carbonyl Oxygen", J. Amer. Chem. Soc., 87(7) (1965) 1515-1521.

Patel, et al., "Ketalization of ketones with diols catalyzed by metal (IV) phosphates as solid acid catalysts," Journal of Molecular Catalysis A: Chemical 194: 267-271 (2003).

Piantadosi, et al., "The Preparation of Cyclic Glycerol Acetals by Transacetalation," Journal of the American Chemical Society 80: 6613-6617 (1958).

Showier, et al., "Condensation Products of Glycerol with Aldehydes and Ketones. 2-Substituted m-Dioxan-5-OLS and 1,3-dioxolane-4-methanols," Chem. Rev. 67: 427-440 (1967).

Smith, et al., "The gem-Dialkyl Effect. III. Kinetic and Equilibrium Studies of Steroid Cyclic Ketal Formation and Hydrolysis," Journal of the American Chemical Society 90(5): 1253-1257 (1968).

Sodergard, et al., "Properties of lactic acid based polymers and their correlation with composition," Prog. Polym. Sci. 27: 1123-1163 (2002).

Vermylen, et al., "Study of the Thermal Evolution of the Cyclic-Oligomer Formation in a Cyclic-Oligomer-Free PET," Journal of Polymer Science: Part A: Polymer Chemistry 38: 416-422 (2000).

Wang, et al., "An efficient procedure for protection of carbonyls catalyzed by sulfamic acid," Journal of Molecular Catalysis A: Chemical 233: 121-126 (2005).

Wood, et al., "Cyclic polyesters: 1. Preparation by a new synthetic method, using polymer-supported reagants," Polymer 34(14): 3052-3058 (1993).

Xu, et al., "The monoblocking of symmetrical diketones on insoluble polymer supports," Can. J. Chem. 61: 1405-1409 (1983).

Yamada, Tatsuhiko et al., "Characterization of the products resulting from ethylene glycol liquefaction of cellulose", J. Wood Sci. 2001, vol. 47, 458-464.

KETAL COMPOUNDS FROM POLYOLS AND OXOCARBOXYLATES

CROSS-REFERENCE TO RELATED APPLICATION

This application is a National Stage application under 35 U.S.C. §371 to International Application No. PCT/US2008/075225 having an International Filing Date of Sep. 4, 2008, which claims benefit of under 35 U.S.C. §119(e) to U.S. Provisional Patent Application No. 60/935,839 entitled "Bishydroxy alkyl ketal compounds", filed on Sep. 4, 2007, which is incorporated by reference in its entirety herein; this application further claims the benefit of U.S. Provisional Patent Application No. 60/935,838 entitled "Polyketal-ester polyols", filed on September 4, 2007, which is incorporated by reference in its entirety herein; this application further claims the benefit of U.S. Provisional Patent Application No. 60/935,843 entitled "NCO prepolymers", filed on Sep. 4, 2007, which is incorporated by reference in its entirety herein; this application further claims the benefit of the U.S. Provisional Patent Application No. 60/935,882 entitled "Copolyesters of ketal-ester compounds", filed on Sep. 5, 2007, which is incorporated by reference in its entirety herein; this application further claims the benefit of the U.S. Provisional Patent Application No. 60/935,881 entitled "Copolyesters prepared from bishydroxyalkyl ketal compounds", filed on Sep. 5, 2007, which is incorporated by reference in its entirety herein; this application further claims the benefit of the U.S. Provisional patent application Ser. No. 60/935,877 entitled "Polyhydroxy functional polyesters prepared from bishydroxyalkyl ketal compounds", filed on Sep. 5, 2007, which is incorporated by reference in its entirety herein; this application further claims the benefit of the U.S. Provisional patent application Ser. No. 60/935,880 entitled "Polyhydroxy functional polyesters prepared from oligo ketal-ester compounds", filed on Sep. 5, 2007, which is incorporated by reference in its entirety herein; this application further claims the benefit of the U.S. Provisional Patent Application No. 60/935,875 entitled "Thermoplastic polyurethanes prepared from bishydroxyalkyl ketal compounds", filed on Sep. 5, 2007, which is incorporated by reference in its entirety herein; this application further claims the benefit of the U.S. Provisional patent application Ser. No. 60/960,627 entitled "Polymeric levulinic ketals of polyhydric alcohols and their use", filed on Oct. 9, 2007, which is incorporated by reference in its entirety herein.

This application is being filed on 4 Sep. 2008, as a PCT International Patent application in the name of Segetis, Inc., a U.S. national corporation, applicant for the designation of all countries except the US, and Douglas Alan Wicks, Charles Williams, both citizens of the U.S., and Sergey Selifonov, a citizen of the Russian Federation, applicants for the designation of the US only.

This application claims the benefit of U.S. Patent Application No. 60/935,839 entitled "Bishydroxy alkyl ketal compounds", filed on Sep. 4, 2007, which is incorporated by reference in its entirety herein; this application further claims the benefit of U.S. Provisional Patent Application No. 60/935, 838 entitled "Polyketal-ester polyols", filed on Sep. 4, 2007, which is incorporated by reference in its entirety herein; this application further claims the benefit of U.S. Provisional Patent Application No. 60/935,843 entitled "NCO prepolymers", filed on Sep. 4, 2007, which is incorporated by reference in its entirety herein; this application further claims the benefit of the U.S. Provisional Patent Application No. 60/935, 882 entitled "Copolyesters of ketal-ester compounds", filed on Sep. 5, 2007, which is incorporated by reference in its entirety herein; this application further claims the benefit of the U.S. Provisional Patent Application No. 60/935,881 entitled "Copolyesters prepared from bishydroxyalkyl ketal compounds", filed on Sep. 5, 2007, which is incorporated by reference in its entirety herein; this application further claims the benefit of the U.S. Provisional Patent Application No. 60/935,877 entitled "Polyhydroxy functional polyesters prepared from bishydroxyalkyl ketal compounds", filed on Sep. 5, 2007, which is incorporated by reference in its entirety herein; this application further claims the benefit of the U.S. Provisional Patent Application No. 60/935,880 entitled "Polyhydroxy functional polyesters prepared from oligo ketal-ester compounds", filed on Sep. 5, 2007, which is incorporated by reference in its entirety herein; this application further claims the benefit of the U.S. Provisional Patent Application No. 60/935,875 entitled "Thermoplastic polyurethanes prepared from bishydroxyalkyl ketal compounds", filed on Sep. 5, 2007, which is incorporated by reference in its entirety herein; this application further claims the benefit of the U.S. Provisional Patent Application No. 60/960,627 entitled "Polymeric levulinic ketals of polyhydric alcohols and their use", filed on Oct. 9, 2007, which is incorporated by reference in its entirety herein.

TECHNICAL FIELD

The present disclosure relates to the preparation of ketal compounds from triols and oxocarboxylic acids or esters thereof, and polymeric materials prepared from the ketal compounds.

BACKGROUND

Many known chemical products such as surfactants, plasticizers, solvents, and polymers are currently manufactured from non-renewable, expensive, petroleum-derived or natural gas-derived feedstock compounds. High raw material costs and uncertainty of future supplies requires the discovery and development of surfactants, plasticizers, solvents, and polymers that can be made from inexpensive renewable biomass-derived feedstocks and by simple chemical methods. Certain polyol compounds can be inexpensive and renewable compounds that are readily available. Oxocarboxylic acids such as pyruvic, acetoacetic, and levulinic acid (and related useful derivatives such as esters) represent another abundant feedstock that is prepared on an industrial scale. Chemical products produced from these two types of materials can fill a need for inexpensive, renewable consumer and industrial products not based on petroleum or other nonrenewable resource.

SUMMARY

Ketal compounds can be prepared from a triol and an oxocarboxylic acid or derivative thereof. The details of one or more embodiments of the invention are set forth in the description below. Other features, objects, and advantages of the invention will be apparent from the description and from the claims.

DETAILED DESCRIPTION

The present disclosure provides a series of triol-derived compounds that are based on the formation of a ketal or acetal of an oxocarboxylate. Such compounds can be produced by reacting approximately one molar equivalent of triol with approximately one molar equivalent of oxocarboxylate in the presence of a catalyst, and under conditions obtaining or allowing for removal of water, typically by distillation. Such ketal compounds include structure (1a):

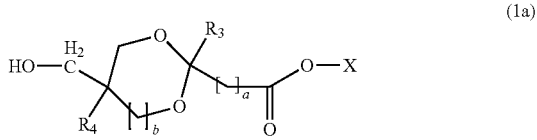

(1a)

wherein a is 0 or 1, b is 0 or 1, $R_3$ is hydrogen or an alkyl group having between 1 and 12 carbons, $R_4$ is an alkyl group having between 1 and 12 carbons, and X is any substituent. Substituents $R_3$ and $R_4$ may further be substituted with one or more functional groups, such as halogen, ether, cyano, and the like.

Such compounds also include those having structure (1b):

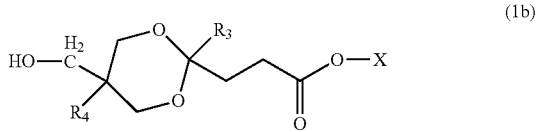

(1b)

wherein $R_3$ is hydrogen or an alkyl group having between 1 and 12 carbons, $R_4$ is an alkyl group having between 1 and 12 carbons, and X is any substituent. Substituents $R_3$ and $R_4$ may further be substituted with one or more functional groups, such as halogen, ether, cyano, and the like.

The compounds of the invention have, in embodiments, one or more isomers. Where an isomer can exist, it should be understood that the invention embodies all isomers thereof, including stereoisomers, conformational isomers, and cis, trans isomers; isolated isomers thereof; and mixtures thereof.

Where $R_3$ is hydrogen, the compounds are acetals. Where $R_3$ is an alkyl group, the compounds are ketals. For the purpose of the invention, both acetals and ketals are referred to as "ketals" for brevity. The formation of ketals is preferably carried out using the methods outlined in U.S. Patent Application No. 61/048,339, the contents of which are incorporated herein in their entirety. However, other methods, such as those set forth in WO 2007/062118A2, may also be used. The preferable method of making the compounds of the invention depend on the exact structures employed in the synthesis.

During the course of the reaction between about one equivalent of triol and one equivalent of oxocarboxylate, two equivalents of water are formed. Water can conveniently be removed by distillation, or by an azeotropic distillation in the presence of a suitable inert solvent such as hexane, heptane, toluene, benzene, and the like.

Suitable examples of triols that are useful in forming the ketals of oxocarboxylates include 1,2,3-propanetriol (glycerol), 1,1,1-trimethylolpropane, 1,1,1-trimethylolethane, 1,2,3-butanetriol, 1,3,4-butanetriol, 1,2,4-butanetriol, 1,2,3-heptanetriol, 4-menthane-1,7,8-triol, 1,2,5-trihydroxypentane, 1,2,6-trihydroxyhexane, 1,2,7-trihydroxyheptane, 1,2,3-trihydroxyoctane, 1,2,3-trihydroxynonane, 1,2,4-trihydroxynonane, 1,2,3-trihydroxyundecane, 1,2,3-trihydroxydodecane, 1,2,11-trihydroxyundecane, 1,2,12-trihydroxydodecane, and the like. In some embodiments, glycerol, 1,1,1-trimethylolpropane, and 1,1,1-trimethylolethane are preferred triols.

Suitable oxocarboxylates employed to make the ketal compounds include, for example, keto acids such as pyruvic acid, acetoacetic acid, levulinic acid, 5-aminolevulinic acid, oxaloacetic acid, α-ketobutyric acid, α-ketoglutaric acid, α-ketoisovaleric acid, 5-ketohexanoic acid, α-ketoisocaproic acid, α-ketoadipic acid, 3-ketoadipic acid, 2-keto-4-methylthiobutyric acid, 4-acetylbutyric acid, 2-keto-3-bromobutyric acid, phenylpyruvic acid, 2-keto-3-phenylpropanoic acid, 2-ketopentanoic acid, 3-ketohexanoic acid, 4-ketohexanoic acid, 2-ketooctanoic acid, 3-ketooctanoic acid, 4-ketooctanoic acid, 7-ketooctanoic acid, 2-keto-4-pentenoic acid, 13-keto-9,11-octadecadienoic acid, 4-ketostearic acid, 9-ketopalmitic acid, 4-ketoheptanedioic acid, penicillic acid, 8-keto-8-aminopelargonic acid, 2-keto-5-aminovaleric acid, 2-succinylamino-6-oxoheptanedioic acid, 2-oxo-3-butynoate, 3-keto-6-acetamidohexanoate, and the like. Additionally, a keto acid may contain hydroxyl or mercapto functionality provided it is protected, e.g. by one or more trimethylsilyl or t-butyl groups, or one or more other protecting groups known to those of skill in the art.

Other suitable oxocarboxylates include semialdehydes such as aspartic semialdehyde, 4-oxobutanoic acid, 5-oxopentanoic acid, 6-oxohexanoic acid, 7-oxoheptanoic acid, α-formylglycine, 3-oxo-2-(phosphonooxy)-propanoic acid (tartronic semialdehyde wherein the hydroxyl group is protected by phosphate), 3-oxopropanoic acid (malonic semialdehyde), 2-methyl-3-oxopropanoic acid (methylmalonic semialdehyde), succinic semialdehyde, adipic semialdehyde, 5-glutamyl semialdehyde, allysine, 2-aminomuconic semialdehyde, 4-amino-5-oxopentanoic acid, N-acetylglutamic semialdehyde, 2-amino-3-(3-oxoprop-1-enyl)-but-2-enedioic acid, and N3-succinyl-L-glutamic-5-semialdehyde.

Also useful in forming the ketal compounds are the esters of the above described oxocarboxylic acids. An oxocarboxylate ester moiety is, in embodiments, a linear, branched, or cyclic alkyl or alkenyl group having 1 to 18 carbon atoms, or an aryl or alkaryl group, wherein the alkyl, alkenyl, aryl, or alkaryl groups can have one or more additional functional groups that can include, for example, halogen, ester, amide, amine, thiol, ether, or silane functionalities and are not particularly limited except that the one or more additional functional groups do not include hydroxyl or mercapto functionality. Suitable ester moieties include methyl or ethyl; a linear or branched isomer of an alkyl group such as propyl, butyl, pentyl, hexyl, septyl, octyl, nonyl, decyl, undecyl, dodecyl, tetradecyl, cetyl, or stearyl; a cycloalkyl group such as cyclohexyl, cyclooctyl, norbornyl, and the like; an alkynyl group such as ethynyl, 3-methylpent-1-yn-3-yl, tetradec-9-yn-1-yl, and the like; an aryl and alkaryl group such as phenyl, benzyl, tolyl, xylyl, 5-phenylpent-1-yl, and the like; wherein the alkyl, alkenyl, alkynyl, aryl, or alkaryl may additionally have one or more functional groups, for example, 1,1,1-trichloro-2-methyl-2-propyl, 5-fluoro-1-pentyl, 5-amino-1-pentyl, 5-benzyloxy-1-pentyl, 5-methoxy-1-pentyl, 3-nitro-2-pentyl, 4-methylthio-1-butyl, 1-carboxyhex-6-yl, propionamid-2-yl, and the like. The ester moiety includes, in some embodiments, a protecting group, such as trimethylsilyl, phosphonooxy, or a phosphatidyl group. The composition of the ester moiety is not particularly limited in its composition.

In some embodiments of the invention, esters of levulinic acid, pyruvic acid, or acetoacetic acid are employed as the oxocarboxylate. For example, ethyl levulinate, ethyl pyruvate, methyl acetoacetate, or n-butyl levulinate can be employed in embodiments of the invention The structures (1a) and (1b) can be reacted to remove one or more equivalents of HOX, wherein X is hydrogen or lower alkyl, to generate polymers having structures (2a) and (2b):

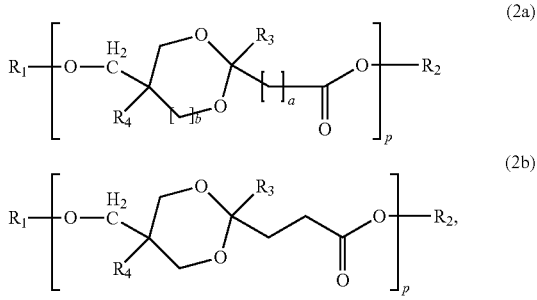

wherein $R_1$ and $R_2$ are ester residues and can be hydrogen or a carboxyl atom of a keto acid fragment, and wherein $R_2$ is hydroxyl, an oxygen atom of a triol, or an oxygen atom of an esterified triol fragment, and wherein p is an integer obtaining substantial useful polyester molecular weight, a is 0 or 1, b is 0 or 1, $R_3$ is hydrogen or an alkyl group having between 1 and 12 carbons, and $R_4$ is hydrogen or an alkyl group having between 1 and 12 carbons. Substituents $R_1$, $R_2$, $R_3$ and $R_4$ may further be substituted with one or more functional groups, such as halogen, ether, cyano, and the like.

The product is a polymer that is, in the absence of other compounds and impurities, typically terminated at its opposite ends by an oxocarboxylate moiety and by an ester fragment.

The value of p depends on many factors and may vary significantly, depending on how much water has been removed, the reactant ratio, acid catalyst and severity of the heating conditions used to remove water. The purity of the reactants are also factors. Relatively impure industrial grades give adducts wherein p is in a range typically between 1 and 10. In other embodiments, p is between 10 and 100; in still other embodiments, p is greater than 100.

Synthesis of the polymeric ketal adducts comprising the structures (2a) or (2b) is carried out in a reaction mixture of fully miscible compounds. For industrial practice, the materials do not need to be anhydrous and thus may contain varying amounts of water. However, it is preferred that these starting materials do not contain excessive amounts of water, as this results in a less efficient use of equipment. Typically, water contents of about 10% or less are preferred.

Synthesis of the polymeric ketal adduct comprising the repeat unit of formula (2a) or (2b) typically requires the presence of a suitable acid catalyst. The term "acid" or "acid catalyst" refers generally to either Lewis or Brønsted-Lowry acids. In embodiments, acid catalysts that are known homogeneous catalysts for either ketal or acetal formation or esterification or transesterification reactions are suitable acid catalysts for use with the method of the invention. The method of the invention is not particularly limited as to the particular species of acid catalyst employed. In embodiments, the acid catalysts employed in the method of the invention are strong protic acid catalysts. Strong protic acids (Brønsted-Lowry acids) are those that have a $K_a$ of 55 or greater. Examples of suitable strong protic acid catalysts include sulfuric acid, arylsulfonic acids and hydrates thereof, such as p-toluenesulfonic acid monohydrate, perchloric acid, hydrobromic acid, and hydrochloric acid. In other embodiments, the acid catalysts employed in the method of the invention are weak protic acid catalysts. Weak protic acids are those having a $K_a$ of less than 55. Examples of suitable weak protic acid catalysts include phosphoric acid or orthophosphoric acid, polyphosphoric acid, and sulfamic acid. In other embodiments, the acid catalysts employed in the method of the invention are aprotic, i.e. non-Brønsted-Lowry acids. Such acids are sometimes referred to as Lewis Acids. Such acid catalysts can include, for example, titanium tetrachloride, aluminum trichloride, and boron trifluoride. In some embodiments, more than one type of acid catalyst is used; thus, blends of one or more of the acids mentioned above may be used in a mixture to catalyze the reactions according to the method of the invention.

In some embodiments, the acid catalyst is incorporated into, or onto, or covalently bound to, a solid support material. Resin beads, membranes, porous carbon particles, zeolite materials, and other solid support materials may be functionalized with acid moieties that are, in embodiments, covalently bound or strongly sorbed to one or more surfaces of the solid support. In a nonlimiting example, sulfonated resin is used in embodiments of the invention, which provide active sulfonic acid groups that are covalently bonded to the resin.

In embodiments, reactions employing the method of the invention may be carried out in the absence of catalyst. In some embodiments, the ketalization or acetalization reaction in the absence of acid catalyst is considerably slower, and higher temperatures may be required to achieve significant levels of conversion. However, when the ketalization or acetalization reaction is carried out in the absence of acid catalyst, the resulting product is substantially acid free and thus useful for direct subsequent polymerizations, transesterifications, or other reactions that employ catalysts sensitive to the presence of an acid. Non-limiting examples of acid sensitive catalysts include titanium alkoxides, alkyl tin alkoxides such as dibutyltin methoxide, or other metal alkoxides, alkyl metal acetylates such as dibutyltin diacetate and dibutyltin dilaurate, metal hydroxides, metal oxides, metal triflates, or halogenated metals such as boron trifluoride or aluminum trichloride.

It is preferred that the condensation be accelerated by use of a catalyst and elevated temperature sufficient to remove water from the reaction mixture without undue time expenditure. The condensation reaction may optionally also be carried out under reduced pressure to facilitate removal of water, and to minimize formation of discolored by-products. One of ordinary skill in the art can practice many variations on the part of the catalyst composition and the amounts used in the preparation described herein. It is preferred that low-cost catalysts that impart minimal or negligible corrosion effects on the equipment used in the synthesis, and have low volatility, toxicity, and environmental impacts, or can be easily neutralized to innocuous compounds, are used. Sulfuric acid is one such preferred catalyst.

The homopolymers of the invention, as well as other polymers of the invention described below wherein various ketal compounds are incorporated into other embodiments of polymeric species, have unique properties that are differentiated from other polymers, even from other polyesters. The various polymers of the invention are also surprisingly thermally and hydrolytically stable. Conventional art ketal compounds are typically less thermally and hydrolytically stable than acetal compounds; however, the polymers of the invention are thermally and hydrolytically stable compared to what one of ordinary skill would expect. Thus, the polymers of the invention as described below are useful for a number of applications, even applications where high temperatures are encountered; the polymers are melt processable, for example, and so may be used in conventional processing equipment such as extruders, injection molders, etc.

Description of First Embodiment

In some embodiments, the compounds of the invention include certain bishydroxyalkyl ketal compounds comprised of materials available from biorenewable sources conforming to a generalized structures (3a), (3b), (4a), or (4b) shown below:

MONO-KETALS

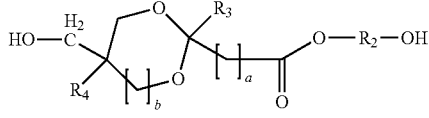
(3a)

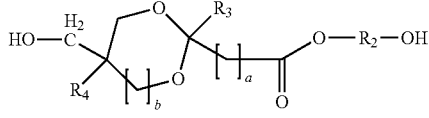
(3b)

BIS-KETALS

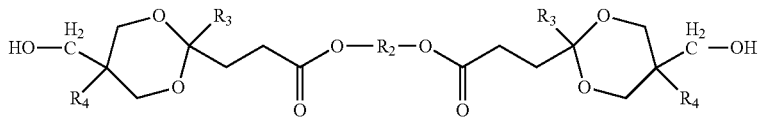
(4a)

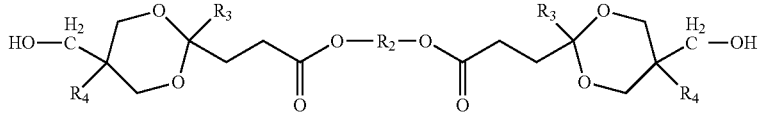
(4b)

wherein:
a equals 0 or 1;
b equals 0 or 1;
$R_2$ represents an alkylene, cycloalkylene or aralkylene group of 2-36 carbons, with the hydroxyl groups attached to saturated carbons, and may contain halogen, ether, ester, carbonate, amide or urethane groups;
$R_3$ is hydrogen or an alkyl group having between 1 and 12 carbons, and may contain halogen, ether, ester, carbonate, amide or urethane groups; and
$R_4$ is hydrogen or an alkyl group having between 1 and 12 carbons, and may contain halogen, ether, ester, carbonate, amide or urethane groups.

These materials can be used for developing products having physical properties suitable for replacing present nonrenewable petrochemical-based polymers for thermoplastics, coatings, elastomers, adhesives, sealants and other industry applications of organic polymers. Such bishydroxyalkyl ketal compounds serve as precursors for polyurethanes, polyester or polycarbonate resins and polyacrylates and are thus used in numerous applications. Due to the products formed on breakdown by acidic hydrolysis these materials will be useful for fabrication or coating of medical devices or as the matrix materials for controlled release of pharmaceutical or agrochemical actives.

The compounds (3a), (3b), (4a), and (4b) can also be used as reactants for thermoset systems in which they react with crosslinking resins such as polyisocyanates, blocked polyisocyanates, polyfunctional epoxides or a methylolated-alkylated amino crosslinker made from one of the following base aminoplasts: urea-formaldehyde, melamine formaldehyde, glycoluril-formaldehyde and benzoguanadine-formaldehyde. These bishydroxyalkyl ketal compounds may also be blended with other hydroxyl functional resins selected from the class consisting of acrylic, polyester, alkyd, polyether, epoxy ester and polyurethane resins and used in thermoset systems with the crosslinking resins described above.

The bishydroxyalkyl ketal monomers are prepared by the sequential reaction of certain dihydric alcohols and trihydric alcohols in the proper ratios with selected oxo-carboxylic acids or esters. Each of these essential starting materials will be discussed in detail herein below. With dihydric and trihydric alcohols added in molar amounts relative to the oxo-carboxylic acid (ester) of 0.5-1.0/1.0 and 1.0/1.0 respectively, a mixture of bishydroxyalkyl ketal compounds, represented by structures (2a), (2b), (3a), and (3b) are obtained after the reaction and removal of the evolved water or monofunctional alcohols. The bishydroxyalkyl ketal compounds represented by structure (3a) and (3b) can be obtained with a diol/triol/oxo-acid ratio of 0.5/1.0/1.0.

Nonlimiting examples of suitable diols for use in the reactions, corresponding to $R_2(OH)_2$, are, in embodiments, 1,2-ethanediol (ethylene glycol), 1,2-propanediol (propylene glycol), 1,3-propanediol, 2,2-dimethyl-1,3-propanediol (neopentyl glycol), 2-butyl-2-ethyl-1,3-propanediol, 3-mercaptopropane-1,2-diol (thioglycerol), dithiothreitol, 1,2-butanediol, 1,3-butanediol, 1,4-butanediol, 2,3-butanediol, 1,5-pentanediol, 3-methyl-1,5-pentanediol, 1,6-hexanediol, 2-ethyl-1,3-hexanediol, cyclohexane-1,2-diol, cyclohexane-1,4-diol, 1,4-dimethylolcyclohexane, 1,4-dioxane-2,3-diol, 3-butene-1,2-diol, 4-butenediol, 2,3-dibromobutene-1,4-diol, 1,8-octanediol, 1,10-decanediol, 1,12-dodecanediol, benzene-1,2-diol (catechol), 3-chlorocatechol, indane-1,2-diol, tartaric acid, and 2,3-dihydroxyisovaleric acid, diethylene glycol (DEG), triethylene glycol, tetraethylene glycol, dipropylene glycol, tripropylene glycol, tetrapropylene glycol, xylene glycol, 1,3-benzenediol (resorcinol), 1,4-benzenediol (hydroquinone), o, m, or p-benzene dimethanol, o, m, or p-glycol phthalates, o, m, or p-bis-1,2-ethylene glycol phthalates, o, m, or p-bis-1,2-propylene glycol phthalates, o, m, or p-bis-1,3-propylene glycol phthalates, diols prepared by hydrogenation of dimer fatty acids, hydrogenated bisphenol A, hydrogenated bisphenol F, propoxylated bisphenol A, isosorbide, 2-butyne-1,4-diol, 3-hexyne-3,5-diol (SURFYNOL® 82, available from Air Products of Allentown, Pa.) and other alkyne-based polyol products marketed under the SURFYNOL® brand name by Air Products of Allentown, Pa., and polymeric polyols such as polyether polyols based on ethylene glycol, for example CARBOWAX® polyethylene glycols (available from The Dow® Chemical Company of Midland, Mich.), polyether diols and polyols based on propylene glycol or combinations of ethylene glycol and propylene glycol, such as those sold by the The Dow® Chemical Company of Midland, Mich., and polyether glycols such as those produced by the INVISTA™ Company of Wichita, Kans. under the trade name TERETHANE®; polycarbonatediols of varying molecular weights, such as L467m, L600m, and L565m, available from Asahi Kasei Corporation (Tokyo, Japan); polyols based on hydroxylated vegetable oils, such as those sold under the trade name BiOH®, available from the Cargill Company of Wayzata, Minn.; hydroxyl-terminated polybutadienes, such as HTPB R45M, sold by Aerocon Systems of San Jose, Calif., polyols produced by the Everchem Company of Media, Pa., or the Maskimi Polyol Sdn. Bhd. of Kajang, Selango Darul Ehsan, Malaysia, and the polyols employed in the Union Carbide Company (South Charleston, W. Va.) publication by Carey, M. A. et al., "Rapid Method for Measuring the Hydroxyl Content of Polyurethane Polyols" (published on the internet at http://www.polyurethane.org/s_api/doc_paper.asp?CID=1044&DID=4060).

The structures (3a), (3b), (4a), and (4b) are synthesized from the corresponding ketal structures by esterification or transesterification employing standard techniques known in the art. Stoichiometry and choice of catalyst, if any, is adjusted to minimize oligomerization and maximize formation of the ketal polyol. An exemplary method of making structures (3a), (3b), (4a), and (4b) is described in WO 2007/062118A2, the contents of which are incorporated herein in its entirety.

Description of Second Embodiment

In another embodiment of the invention, certain polyketal-ester polyols comprised of materials are available from biorenewable sources and conform to generalized structures (5a) and (5b) shown below:

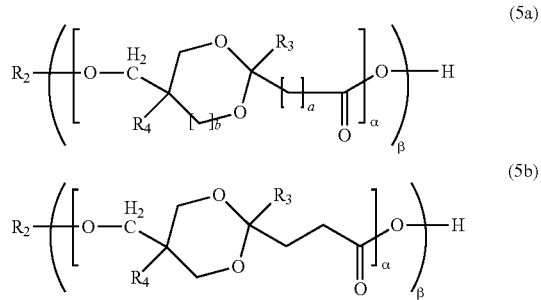

wherein:
a equals 0 or 1;
b equals 0 or 1;
$R_2$ represents an alkylene, cycloalkylene or aralkylene group of 2-36 carbons, with the hydroxyl groups attached to saturated carbons, and may contain halogen, ether, ester, carbonate, amide or urethane groups;
$R_3$ is hydrogen or an alkyl group having between 1 and 12 carbons, and may contain halogen, ether, ester, carbonate, amide or urethane groups;
$R_4$ is hydrogen or an alkyl group having between 1 and 12 carbons, and may contain halogen, ether, ester, carbonate, amide or urethane groups;
$\alpha$ is an integer of about 1 to 100 and represents the average degree of oligomerization and is determined by the ratio of reactants; and
$\beta$ is an integer of 2 to 10.

These materials can be used for developing products having physical properties suitable for replacing present fully petrochemical-based polymers for thermoplastics, coatings, elastomers, adhesives, sealants and other industry applications of organic polymers. Such polyketal-ester polyols may serve as precursors for polyurethanes, polyester or polycarbonate resins and polyacrylates and are thus used in numerous applications.

Such polyketal-ester polyols can also be used as reactants for thermoset systems in which they react with crosslinking resins such as polyisocyanates, blocked polyisocyanates, polyfunctional epoxides or a methylolated-alkylated amino crosslinker made from one of the following base aminoplasts: urea-formaldehyde, melamine formaldehyde, glycoluril-formaldehyde and benzoguanadine-formaldehyde. These bishydroxyalkyl ketal compounds may also be blended with other hydroxyl functional resins selected from the class consisting of acrylic, polyester, alkyd, polyether, epoxy ester and polyurethane resins and used in thermoset systems with the crosslinking resins described above.

For these applications a number average OH equivalent weight of 200 to 5000 is preferred, more preferably between 250 and 1000.

The polyketal-ester polyols are synthesized by transesterification of ketal compounds with polyols $R_2(OH)_s$, where $\beta$ is as described above. Thus, $R_2(OH)_\beta$ represents a polyol having at least two hydroxyl groups. The diols and triols listed above are all suitable polyols for use in the esterification or transesterification reaction to form the polyketal-ester polyols of the invention. Additionally, any of the known tetrols, pentanols, hexanols, or higher polyols are useful in forming the polyketal-ester polyols having structures (4a) and (4b). Such compounds are numerous, as a plethora of commercial monomeric, oligomeric, dendritic, or polymeric polyols having three or more hydroxyl groups per molecule are available.

The group of useful polyols includes diglycerol, pentaerythritol, mannitol, sorbitol, xylitol, threitol, erythrol, erythritol, maltitol, lactitol, raffinose, stachyose, and poly(vinyl alcohol) and copolymers thereof.

The polyketal-ester polyols are prepared by one of two methods, each involving two sequential reaction steps.

Method One: Esterification of preferred trihydric alcohols (triols) with selected oxo-carboxylic acids, preferably pyruvic and acetoacetic acid, at OH/COOH ratios of less than 1, followed by reaction with a equimolar amount (on oxocarboxylate) of a trihydric alcohol with concurrent esterification and ketal formation. Both steps of this reaction can be carried out optionally in a solvent and optionally with the addition of an acidic or metal catalyst, while removing the water of reaction.

Method Two: Formation of ketals by equimolar reaction of a trihydric alcohol in the proper ratios with selected oxo-carboxylic acid or ester. After addition polyhydric alcohol at OH/COX ratios of less than 1, the reaction conditions are set to allow transesterification and the removal of the evolved monofunctional alcohol (X—OH). Both steps of this reaction can be carried out optionally in a solvent and optionally with the addition of an acidic or metal catalyst, while removing the water of reaction.

The catalysts used may be acidic catalysts such as toluenesulfonic acids, preferably organometallic compounds, in particular those based on titanium or tin, such as titanium tetrabutoxide or tin (II) octanoate. Stoichiometry, use of catalyst, and reaction conditions are employed to form oligomers of the desired length and an end product having the desired hydroxyl content.

If desired, monofunctional alcohols and/or carboxylic acids may be used in a mixture with the polyfunctional alcohols and carboxylic acids to adjust the functionality. Examples of monofunctional carboxylic acids include monomeric fatty acids, for example oleic acid or ricinoleic acid. Examples of monomeric alcohols include aliphatic alcohols having from 1 to 15, preferably from 2 to 10, carbon atoms, for example hexanol, octanol, nonanol or decanol.

Description of Third Embodiment

In another embodiment of the invention, certain isocyanate functional prepolymers are prepared from the compounds having the structures (3a), (3b), (4a), (4b), (5a), or (5b) and comprised of materials available from biorenewable sources. Two examples, based on structures (5a) and (5b), are shown below and (6a) and (6b), respectively:

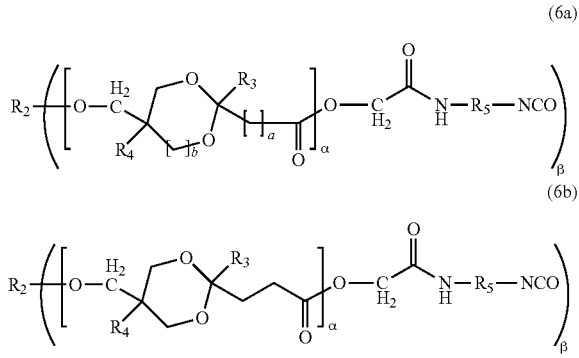

wherein
a equals 0 or 1;
b equals 0 or 1;
$R_2$ represents an alkylene, cycloalkylene or aralkylene group of 2-36 carbons, with the hydroxyl groups attached to saturated carbons, and may contain halogen, ether, ester, carbonate, amide or urethane groups;
$R_3$ is hydrogen or an alkyl group having between 1 and 12 carbons, and may contain halogen, ether, ester, carbonate, amide or urethane groups;
$R_4$ is hydrogen or an alkyl group having between 1 and 12 carbons, and may contain halogen, ether, ester, carbonate, amide or urethane groups;
$R_5$ is an organic group obtained by removing the isocyanate groups from an organic diisocyanate having a molecular weight of about 112 to 1,000, preferably about 140 to 400;
$\alpha$ is an integer of about 1 to 100 and represents the average degree of oligomerization and is determined by the ratio of reactants; and
$\beta$ is an integer of 2 to 10.

It will be appreciated that any of the compounds (3a), (3b), (4a), and (4b) may be similarly functionalized to form isocyanate prepolymers of the invention.

Such isocyanate functional prepolymers have utility in the preparation of adhesives, coatings, elastomers and sealants for a wide range of industrial applications. Due to the biocompatibility of the major products formed on breakdown by acidic hydrolysis, these materials will be useful for fabrication or coating of medical devices or as the matrix materials for controlled release of pharmaceutical or agro-chemical actives. They may also serve as building blocks for the preparation of thermoplastic polyurethanes or polyurethane dispersions.

The ketal-ester polyols used in this invention are prepared by the reaction of polyketal-esters having structures (4a) or (4b) with diisocyanates having the structure

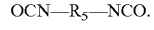

Non-limiting examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)methane, 2,4'-dicyclohexyl-methane diisocyanate, 4,4'-dicyclohexyl-methane diisocyanate, 1,3-bis-(isocyanatomethyl)-cyclohexane, 1,4-bis-(isocyanatomethyl)-cyclohexane, bis-(4-isocyanato-3-methyl-cyclohexyl)methane, $\alpha,\alpha,\alpha',\alpha'$-tetramethyl-1,3-xylylene diisocyanate, $\alpha,\alpha,\alpha',\alpha'$-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, 1,5-diisocyanato naphthalene; and mixtures thereof.

In accordance with the present invention the polyisocyanate component may also be in the form of a polyisocyanate adduct. Suitable polyisocyanate adducts are those containing isocyanurate, uretdione, biuret, urethane, allophanate, carbodiimide and/or oxadiazinetrione groups.

Synthesis of the isocyanate prepolymers of the invention is carried out using standard techniques wherein a polyol is reacted with a stoichiometric excess of diisocyanate to form an isocyanate capped prepolymer. Such syntheses are widely known and practiced in the industry.

DESCRIPTION OF FOURTH EMBODIMENT

In another embodiment of the invention, certain copolyesters of the ketal compounds of the invention are synthesized using compounds (1a) and (1b) as monomers in a copolyesterification reaction. The copolyesters are available from biorenewable sources conforming to a generalized structure (7a) and (7b) shown below.

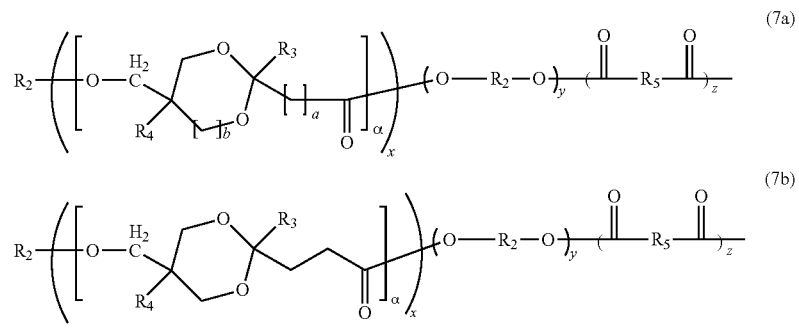

wherein
  a equals 0 or 1;
  b equals 0 or 1;
  $R_2$ represents an alkylene, cycloalkylene or aralkylene group of 2-36 carbons, with the hydroxyl groups attached to saturated carbons, and may contain halogen, ether, ester, carbonate, amide or urethane groups;
  $R_3$ is hydrogen or an alkyl group having between 1 and 12 carbons, and may contain halogen, ether, ester, carbonate, amide or urethane groups;
  $R_4$ is hydrogen or an alkyl group having between 1 and 12 carbons, and may contain halogen, ether, ester, carbonate, amide or urethane groups;
  $R_5$ is an organic group that is the residue of a diacid having a molecular weight of about 100 to 1,000, preferably about 150 to 500;
  $\alpha$ is an integer of about 1 to 100 and represents the average degree of oligomerization and is determined by the ratio of reactants; and
  x, y and z represent the molar fractions of ketal-ester (or oligo ketal-ester), dihydric alcohol, and diacid, respectively, in the copolymer.

These materials can be used for developing products having physical properties suitable for replacing present fully petrochemical-based polymers for thermoplastics, coatings, elastomers, adhesives, sealants and other industrial applications of organic polymers. Due to the biocompatibility of the major products formed on breakdown by acidic hydrolysis, these materials will be useful for fabrication or coating of medical devices or as the matrix materials for controlled release of pharmaceutical or agro-chemical actives.

Such copolyesters are prepared by the condensation of compounds having structures (1a), (1b), (2a), or (2b) with additional diols and diacids. The copolymerization is accomplished by esterification or transesterification of ketal acids and esters thereof according to the invention by employing standard techniques of polyesterification, the same as or similarly to the reaction conditions employed to form the compounds having structures (2a) and (2b). The stoichiometry of the copolymerizations is adjusted according to total hydroxyl number and acid number to obtain the desired degree of polymerization.

Non-limiting examples of suitable diols for use in the copolymerization reactions that result in structures (7a) and (7b) are those listed above. Non-limiting examples of suitable diacids include aliphatic, cycloaliphatic or aromatic dicarboxylic acids, for example, succinic acid, glutaric acid, adipic acid, pimelic acid, suberic acid, azelaic acid, sebacic acid, nonanedicarboxylic acid, decanedicarboxylic acid, terephthalic acid, isophthalic acid, o-phthalic acid, tetrahydrophthalic acid, hexahydrophthalic acid, maleic acid, fumaric acid, naphthalene dioc acid, dimerized fatty acids, or hydrogenated dimerized fatty acids. The methyl, ethyl, propyl, butyl or phenyl esters of the acids listed above are suitable substitutes for the diacid component, as well as acid anhydrides (such as o-phthalic, maleic or succinic acid anhydride or a mixture thereof.

Description of Fifth Embodiment

In another embodiment of the invention, certain copolyesters formed by reacting diacids and optionally other polyhydric alcohols with bishydroxyalkyl ketal compounds comprised of materials available from biorenewable sources and selected from the compounds having structures (3a), (3b), (4a), or (4b). Such structures are similar to (7a) and (7b) above.

These materials can be used for developing products having physical properties suitable for replacing present fully petrochemical-based polymers for thermoplastics, coatings, elastomers, adhesives, sealants and other industrial applications of organic polymers. Due to the biocompatibility of the major products formed on breakdown by acidic hydrolysis, these materials will be useful for fabrication or coating of medical devices or as the matrix materials for controlled release of pharmaceutical or agro-chemical actives.

Description of Sixth Embodiment

In another embodiment of the invention, certain hydroxy functional polyesters are formed whereby the compounds have an average of more than 2OH groups per polymer chain. Such compounds are formed by reacting diacids, polyfunctional acids having more than two acid or ester functionalities per molecule, polyols having more than two hydroxyl groups per molecule, and optionally other dihydric alcohols with compounds comprised of materials available from biorenewable sources and selected from the compounds having structures (3a), (3b), (4a), or (4b).

These materials can be used in thermosetting coatings, adhesives and sealants, acting as polyfunctional coreactants for crosslinking resins such as polyisocyanates, blocked polyisocyanates, polyfunctional epoxides or a methylolated-alkylated amino crosslinker made from one of the following base aminoplasts: urea-formaldehyde, melamine formaldehyde, glycoluril-formaldehyde and benzoguanadine-formaldehyde. These bishydroxyalkyl ketal compounds may also be blended with other hydroxyl functional resins selected from the class consisting of acrylic, polyester, alkyd, polyether, epoxy ester and polyurethane resins and used in thermoset systems with the crosslinking resins described above. Due to the biocompatibility of the major products formed on breakdown by acidic hydrolysis, these materials will be useful for fabrication or coating of medical devices or as the matrix materials for controlled release of pharmaceutical or agro-chemical actives.

Polyfunctional acids that are useful in forming the polyhydroxylated polymers of the invention include, for example, triacids such as 1,3,5-trimethylcyclohexane-1,3,5-tricarboxylic acid, cis or trans aconitic acid, propane-1,2,3-tricarboxylic acid, hemmellitic acid, isocitric acid, and esters thereof.

The polyesters of these embodiments are formed using the same techniques as, for example, the polyesters described in the formation of structures (7a) and (7b), except that the stoichiometry is adjusted to account for the polyfunctional acids employed in the reaction and the higher degree of hydroxyl content desired.

Description of Seventh Embodiment

In another embodiment of the invention, certain thermoplastic polyurethanes are formed by reacting diisocyanates and optionally other dihydric alcohols with bishydroxyalkyl ketal compounds comprised of materials available from biorenewable sources and selected from structures (3a), (3b), (4a), (4b), (5a) or (5b) wherein the value of $\beta$ is 2, (7a), (7b), or structures described in the fifth embodiment and having structures similar to those of (7a) and (7b), provided that the copolyester structures (7a), (7b) have at least two hydroxyl moieties per molecule.

These materials can be used for developing products having physical properties suitable for replacing present fully petrochemical-based polymers for thermoplastics, coatings, elastomers, adhesives, sealants and other industrial applications of organic polymers. Due to the biocompatibility of the major products formed on breakdown by acidic hydrolysis, these materials will be useful for fabrication or coating of medical devices or as the matrix materials for controlled release of pharmaceutical or agro-chemical actives.

In embodiments wherein oligomeric or polymeric ketal compounds such as those having structures (5a) or (5b) wherein =2, (7a), or (7b) are employed, the resulting polymers have polyester blocks linked by urethane moieties.

It has been found that the polyurethanes of the invention can be obtained by mixing appropriate quantities of one or more of the hydroxyl terminated structures (3a), (3b), (4a), (4b), (5a) or (5b) wherein the value of $\beta$ is 2, (7a), (7b), or structures described in the fifth embodiment and having structures similar to those of (7a) and (7b), with various aliphatic and/or aromatic diisocyanate compounds, such as those described in the Third Embodiment, and causing reaction to occur by means of heating and/or with catalysts sufficient to accelerate the reaction. Non-limiting examples of typical catalysts suitable for making the polyisocyanate compounds include dibutyl tin dilaurate, 1,4-diazabicyclo[2.2.2]octane (DABCO™, TED), and the like. The reaction of making a polyisocyanate compound from a polyhydric alcohol comprising the units of formula (6) can be carried out in the presence of an inert solvent, which may optionally be removed at the end of the reaction by distillation.

One or more of the polyhydric alcohol can then be reacted with one or more isocyanate compounds having two or more isocyanate groups per representative molecule, thereby providing for a polyurethane polymer.

Various polyurethane polymers can be prepared and used to manufacture a plethora of polyurethane goods that in a way substantially similar to polyurethane polymers known in the art. Polyurethane polymers can be solid or viscous liquids, rigid or flexible, and they can be prepared as thermoset or thermoplastic polymers. Depending on the specific polymer composition, they can be cast, extruded, or otherwise shaped in a variety of forms needed to manufacture finished polymer goods. The polyurethane polymers can contain various additives known in the art, such organic or inorganic fillers, pigments, stabilizers, anti-oxidants, and lubricants The polyurethane polymers disclosed herein are made with use of low-cost renewable monomers to provide the predominant part of the weight of the resulting polymers, thereby offering a cost advantage when compared to the known in the art polyurethanes made predominantly or exclusively with use of non-renewable petroleum- or coal-derived monomers.

The polyurethane polymers also recyclable at the monomer level. If so desired, at the end of their useful life, the polyurethane polymers can be treated by a trans-esterification reaction, to allow for the decomposition of the polymers and the formation of one or more predecessor monomers which can be recovered, purified and re-used.

Description of the Eighth Embodiment

In another embodiment of the invention, certain polyurethanes are formed by reacting polyisocyanates available from biorenewable sources and selected from structures (6a) or (6b) with a polyhydric alcohol. The polyhydric alcohols are those having at least two hydroxyl moieties and are diols, triols, tetrols, and higher polyols such as those described in various embodiments above. A plethora of polyols are commercially available for reaction with polyisocyanates, as will be readily understood by those of ordinary skill.

These polyurethanes can be used for developing products having physical properties suitable for replacing present fully petrochemical-based polymers for thermoplastics, coatings, elastomers, adhesives, sealants and other industrial applications of organic polymers. Due to the biocompatibility of the major products formed on breakdown by acidic hydrolysis, these materials will be useful for fabrication or coating of medical devices or as the matrix materials for controlled release of pharmaceutical or agro-chemical actives.

It has been found that the polyurethanes of the invention can be obtained by mixing appropriate quantities of one or more of the polyisocyanates having structures (6a) or (6b) with various aliphatic and/or aromatic polyols, and causing reaction to occur by means of heating and/or with catalysts sufficient to accelerate the reaction. Non-limiting examples of typical catalysts suitable for making the polyisocyanate compounds include dibutyl tin dilaurate, 1,4-diazabicyclo[2.2.2]octane (DABCO™, TED), and the like. The reaction of making a polyurethane can be carried out in the presence of an inert solvent, which may optionally be removed at the end of the reaction by distillation.

Various polyurethane polymers can be prepared and used to manufacture a plethora of polyurethane goods that in a way substantially similar to polyurethane polymers known in the art. Polyurethane polymers can be solid or viscous liquids, rigid or flexible, and they can be prepared as thermoset or thermoplastic polymers. They are, in embodiments, prepared as foams that are open celled or close celled foams. Depending on the specific polymer composition, they can be cast, extruded, or otherwise shaped in a variety of forms needed to manufacture finished polymer goods. The polyurethane polymers can contain various additives known in the art, such organic or inorganic fillers, pigments, stabilizers, anti-oxidants, and lubricants The polyurethane polymers disclosed herein are made with use of low-cost renewable monomers to provide the predominant part of the weight of the resulting polymers, thereby offering a cost advantage when compared to the known in the art polyurethanes made predominantly or exclusively with use of non-renewable petroleum- or coal-derived monomers.

The polyurethane polymers are also recyclable at the monomer level. If so desired, at the end of their useful life, the polyurethane polymers can be treated by a trans-esterification reaction, to allow for the decomposition of the polymers and the formation of one or more predecessor monomers which can be recovered, purified and re-used.

Description of Ninth Embodiment

In embodiments, certain polyurethanes are formed by reacting hydroxy functional polyesters with an average of more than 2OH groups per polymer chain and having the structures described in the Sixth Embodiment above, with a diisocyanate such as any of those described in the Third Embodiment above. Such polyurethanes are branched or crosslinked and are synthesized using the techniques described in the Eighth Embodiment above.

For use in polyurethane synthesis, the polymers described in the Sixth Embodiment are, in embodiments, prepared by carrying out the polymerization reaction so that polymerization product has preferably an average molecular weight in excess of 500 Da, more preferably, in excess of 1000 Da, and has an average of more than two hydroxyl groups. The resulting polymerization product can be a linear, branched, cross-linked, or star-shaped polymer. One or more of such polymerization product can then be used as polyol compounds in a reaction with one or more isocyanate compounds having two or more isocyanate groups.

By employing the embodiments as described, various polyurethane polymers are, in embodiments, prepared and used to manufacture a plethora of polyurethane goods that in a way substantially similar to polyurethane polymers known in the art. Polyurethane polymers can be solid or viscous liquids, rigid or flexible, and they can be prepared as thermoset or thermoplastic polymers; they may be foamed such that open or closed cell foams are formed. Depending on the specific polymer composition, they can be cast, extruded, or otherwise shaped in a variety of forms needed to manufacture finished polymer goods. The polyurethane polymers can contain various additives known in the art, such organic or inorganic fillers, pigments, stabilizers, anti-oxidants, and lubricants The polyurethane polymers disclosed herein are made with use of low-cost renewable monomers to provide the predominant part of the weight of the resulting polymers, thereby offering a cost advantage when compared to the known in the art polyurethanes made predominantly or exclusively with use of non-renewable petroleum- or coal-derived monomers.

The polyurethane polymers also recyclable at the monomer level. If so desired, at the end of their useful life, the polyurethane polymers can be treated by a trans-esterification reaction, to allow for the decomposition of the polymers and the formation of one or more predecessor monomers which can be recovered, purified and re-used.

The polymers of the invention, as described in the Second, Fourth, Fifth, Sixth, Seventh, Eighth, and Ninth Embodiments, are, in embodiments, employed in a wide variety of industrially useful and significant applications. The polymers of the invention are, in embodiments, used in blends, optionally obtained by reactive extrusion. Blends include blends of various species of the polymers of the invention as well as blends with such polymers as aliphatic/aromatic copolyesters, as for example polybutylene terephthalate adipate (PBTA), polybutylene terephthalate succinate (PBTS), and polybutylene terephthalate glutarate (PBTG); biodegradable polyesters such as polylactic acid, poly-$\epsilon$-caprolactone, polyhydroxybutyrates such as poly-3-hydroxybutyrates, poly-4-hydroxybutyrates and polyhydroxybutyrate-valerate, polyhydroxybutyrate-propanoate, polyhydroxybutyrate-hexanoate, polyhydroxybutyrate-decanoate, polyhydroxybutyrate-dodecanoate, polyhydroxybutyrate-hexadecanoate, polyhydroxybutyrate-octadecanoate, and polyalkylene succinates and their copolymers with adipic acid, lactic acid or lactide and caprolactone and their combinations, and the like; polystyrene and copolymers thereof; polyurethanes; polycarbonates; polyamides such as Nylon 6 and Nylon 6,6; polyolefins such as polyethylene, polypropylene, and copolymers thereof; or any other industrially useful polymeric compounds. Blends also include, in some embodiments, composites with gelatinized, destructed and/or complexed starch, natural starch, flours, and other materials of natural, vegetable or inorganic origin. The polymers of the invention are, in some embodiments, blended with polymers of natural origin, such as starch, cellulose, chitosan, alginates, natural rubbers or natural fibers (such as for example jute, kenaf, hemp). The starches and celluloses can be modified, such as starch or cellulose esters with a degree of substitution of between 0.2 and 2.5, hydroxypropylated starches, or modified starches with fatty chains, among others.

The polymers according to the invention, and blends of thereof, possess properties and values of viscosity that render them suitable for use, by appropriately adjusting the molecular weight, in numerous practical applications, such as films, injection-molded products, extrusion coated products, fibers, foams, thermoformed products, extruded profiles and sheets, extrusion blow molding, injection blow molding, rotomolding, stretch blow molding and the like.

In the case of films, production technologies like film blowing, casting, and coextrusion can be used. Moreover such films can be subject to monoaxial or biaxial orientation in line or after film production. It is also possible that the stretching is obtained in presence of an highly filled material with inorganic fillers. In such a case, the stretching can generate micropores and the so obtained film can be suitable for hygiene applications.

The polymers according to the invention are suitable for the production of films. A "film" is defined, for the purposes of the invention, as a sheet type material that is flexible to e.g. bending and is between about 1 µm to 5 mm thick. Films employing the polymers of the invention are, in embodiments, one-directional or two-directional, single layer or multilayer, and employ the polymers of the invention as a single component or in a blend with other materials, as described above. The films are useful for various applications including agricultural mulching films; printable films for graphics or text; cling films (extensible films) for foodstuffs, films for bales in the agricultural sector and for wrapping of refuse; shrink films such as for example for pallets, mineral water, six pack rings, and so on; bags and liners such as for collection of refuse, holding foodstuffs, gathering mowed grass and yard waste, and the like; thermoformed single-layer and multilayer packaging for foodstuffs, such as for example containers for milk, yogurt, meat, beverages, etc.; and in multilayer laminates with layers of paper, plastic materials, aluminum, metalized films for a wide variety of applications.

The polymers of the invention are also useful for coatings that form a layer on top of a film, an article, and the like. Coatings of the invention are applied, in embodiments, by extrusion coating, die coating, slot coating, brush coating, spray coating, or any other generally known technique employed in the coating industry. Coatings employing the polymers of the invention are useful as protective coatings, paint components, adhesives or glues, barrier layers, and the like. The coatings of the invention are applied, in embodiments, with or without additional solvent(s), such as coalescing solvents, and with our without additives such as UV blocking agents, antibacterial agents, colorants, fillers, and the like. The coatings of the invention are, in some embodiments, crosslinked after application.

The polymers of the invention are also useful in forming articles. An "article", as defined for the purposes of the invention, includes objects that are be rigid or flexible; that exist as standalone objects or as part of an assembly or laminate; and that include one or more polymers of the invention or a blend thereof, optionally with one or more additional materials. Some examples of useful articles that include polymers of the invention are punnets for foodstuffs, 1-beams for construction, casings for e.g. pens, computer screens, and the like; parts for automobile construction, table tops, and the like; decorative items such as lamp parts, jewelry, vases, architectural features, and the like; children's toys; drink bottles; and many other articles. The invention is not particularly limited in terms of what articles may be formed employing the polymers of the invention.

Articles that can be formed include foamed articles. Foaming of polyurethanes are discussed above; those techniques and others generally known in the industry are used, in embodiments, to form foamed articles from the various polymers of the invention. Foamed articles include both rigid and flexible foams. Some examples of useful foamed materials include cushions for automobile seats, interior or exterior furniture, and the like; foamed or foamable beads for the production of pieces formed by sintering; foamed blocks made up of pre-foamed particles; foamed sheets, thermoformed foamed sheets, and containers obtained therefrom for the packaging of foodstuffs.

Articles also include fibrous articles. Examples of fibrous articles include standard scale fibers, microfibers, nanofibers, and composite fibers. Composite fibers have, in embodiments, a core constituted by a rigid polymer such as PLA, PET, PTT, etc. and an external shell made with one or more polymers of the invention; other composite fibers have various section configurations (from round to multilobed). Fibers also include flaked fibers, woven and non-woven fabrics or spun-bonded or thermobonded fabrics for the sanitary sector, the hygiene sector, the agricultural sector, georemediation, landscaping and the clothing sector.

The following Examples further elucidate and describe the compounds of the invention without limiting the scope thereof.

EXPERIMENTAL SECTION

Analytical Procedures

Gas Chromatography (GC) and GC-Mass Spectrometry (GC-MS) Analyses

GC and GC-MS analyses are carried out according to standard laboratory techniques. Standard GC analysis is carried out by flame ionization detector; GC-MS employs a mass spectrometer instead of a flame ionization detector, to. The integration peak areas of all peaks in the chromatogram are automatically calculated by an Agilent Technologies ChemStation (Agilent Technologies of Santa Clara, Calif.). The calculated peak areas are reported as a weighted percent (expressed as abundance) relative to the area of all of the detected peaks in the chromatogram (total area). These calculations are used elsewhere herein to report all percent yield, percent yield "based on theoretical", percent yield "as determined by GC-MS", and any other percent reaction statements resulting from GC or GC-MS analyses.

Gel Permeation Chromatography (GPC)

Molecular weight determination is carried out by GPC using a Waters Isocratic HPLC System (from Waters Corp. of Milford, Mass.) that includes a Waters 2414 Differential Refractometer, Waters 1515 Isocratic Pump, Waters 717 Autosampler, and Waters Column Heater and Empower GPC Software for molecular weight analysis. For samples with an expected molecular weight of 20,000-400,000 Daltons a PLgel Mixed D 5 µm column, 300×7.5 mm, is used; for samples with an expected molecular weight of less than 20,000 a PLgel Mixed E 5 µm column, 300×7.5 mm, is used; and for samples with an expected molecular weight between 20,000 and 2,000,000 a PLgel Mixed C 5 µm column, 300× 7.5 mm is used. All columns were obtained from Polymer Labs, a division of Varian Inc. of Palo Alto, Calif. THF mobile phase is employed at 1 ml/min and weight average molecular weight ($M_w$) is calculated against polystyrene narrow molecular weight standards.

Differential Scanning Calorimetry (DSC)

Glass transition temperature is determined by DSC following ASTM D-3418, employing a TA Q200 instrument with refrigerated cooling and TA Thermal Advantage software (from TA Instruments of New Castle, Del.). Homogeneous samples of between about 5 and 15 mg are prepared, weighed, placed in a Tzero pan and crimped with a Tzero lid, (pan and lid both available from TA Instruments). The mass of the sample is entered into the Thermal Advantage software. The thermal analysis is carried out according to one of the two sets of parameters below:

Parameter Set 1
Cycle 0: Equilibrate at −80° C.
Isotherm for 2.00 minutes
End of Cycle 0
Cycle 1: Ramp 10° C./min to 150° C.
Isotherm for 2.00 minutes
End of Cycle 1
Cycle 2: Ramp 10° C./min to −80° C.
Isotherm for 2.00 minutes
End of Cycle 2
Cycle 3: Ramp 10° C./min to 150° C.
Isotherm for 2.00 minutes
End of Cycle 3
Repeat at Cycle 0
Parameter Set 2
Cycle 0: Equilibrate at −150° C.
Isotherm for 5.00 minutes
End of Cycle 0
Cycle 1: Ramp 10° C./min to 150° C.
Isotherm for 5.00 minutes
End of Cycle 1
Cycle 2: Ramp 10° C./min to −150° C.
Isotherm for 5.00 minutes
End of Cycle 2
Cycle 3: Ramp 10° C./min to 150° C.
Isotherm for 5.00 minutes
End of Cycle 3 Repeat at Cycle 0

Thermogravimetric Analysis (TGA)

TGA is conducted utilizing a TA Q50 with TA Thermal Advantage software (from TA Instruments of New Castle, Del.). A homogeneous sample weighing approximately 30 milligrams is placed into the TGA platinum sample pan. Samples are analyzed under a nitrogen atmosphere. The TGA temperature profile is listed below:
Equilibrate at 30° C.
Ramp 10° C./min to 800° C.

Hydroxyl Number

Hydroxyl numbers are determined according to ASTM E1899-02 (2002).

Isocyanate Number

Isocyanate number is determined using the procedure outlined in ASTM D2572-87 (1987), except that the solvent used is DMF instead of toluene and 25 ml of isopropanol is used to solubilize the bromophenyl indicator rather than the 100 ml isopropanol as prescribed by the procedure.

Dynamic Mechanical Analysis (DMA)

DMA is conducted utilizing a TA Q800 with liquid nitrogen cooling with TA Thermal Advantage software (from TA Instruments of New Castle, Del.). A uniform sample is prepared to fit the appropriate sample mounting clamp (extension, dual cantilever, compression, etc.). The appropriate sample dimensions are measured and entered into the Thermal Advantage software. Typical experimental run conditions are listed below:
Strain 0.1%
Frequency 1 Hz
Force Track 125%
Equilibrate at −100° C.
Isotherm for 5 min.
Ramp 3° C./min to 200° C.

Rheological Characterization

The viscosity of a material is determined by Brookfield viscometry, using a Brookfield DV2+Pro viscometer (available from the Brookfield Engineering Laboratories of Middleborough, Mass.). The appropriate spindle is chosen dependent on sample viscosity. Samples are analyzed at 25° C. unless a different temperature is stated.

Example 1

Trimethylolpropane Ketal of Ethyl Levulinate ("EtLTMPK")

A 2 liter, single neck round bottom flask was equipped with a stir bar and charged with 873.90 g (6.07 mol) of ethyl levulinate (obtained from Langfang Triple Well Chemicals Company, Ltd. Of Langfang City, HeBei, China), 407.5 g (3.04 mol) 1,1,1-trimethylolpropane (obtained from the Sigma-Aldrich Company of St. Louis, Mo.) and 16.4 μl (0.304 mmol) of 98% sulfuric acid (obtained from the Sigma-Aldrich Company). The flask was placed on a rotary evaporator with an oil bath temperature of 75° C. and was subjected to a vacuum of between 10 and 20 torr. The flask was rotated on the rotary evaporator for about 2.5 hours and then the temperature of the oil bath was raised to 90° C. This temperature was maintained for about 1 hour and then the temperature was increased, again, to 100° C. and maintained for 1 hour 45 minutes. The temperature was then raised again to 110° C. and was maintained at that temperature for about 10 minutes. For each step in temperature, the contents of the reaction flask were observed to bubble and a liquid was observed to be condensing on the rotary evaporator. At the point that the bubbling stopped and liquid was observed to stop collecting on the condenser, the next step in temperature was taken.

After the oil bath was maintained at 110° C. for about 10 minutes the flask was removed from the rotary evaporator and the contents of the flask allowed to cool to room temperature. A sample of the crude reaction product was removed from the flask and analyzed by GC. The analysis showed that the contents consisted of about 54.5% of the trimethylolpropane ketal of ethyl levulinate ("EtLTMPK"), about 38.7% ethyl levulinate, about 4.9% trimethylolpropane, and approximately 1% of unknown side reaction products.

Then 654.2 g of the crude reaction product was placed in a 1 liter round bottom flask. Teflon boiling chips and a stir bar were added to the flask. The flask was equipped with a fractionation column, condenser, and vacuum/nitrogen inlet. A vacuum was applied to the flask, with stirring, until the pressure reached about 9 ton. A heating mantle was applied to the flask and the heat setting was set to 7.5 on a scale of 10. After about 1 hour the temperature in the distillation column head was observed to reach 74° C. Over the next 20 minutes the head temperature was fluctuating between 74 and 85° C. and a liquid was observed to condense in the condensation column. Over the following 15 minutes the temperature in the distillation head was observed to slowly rise to 165° C. and a small fraction of the liquid distilling at 165° C. was collected. Then the vacuum was released and the contents of the reaction flask were allowed to cool to room temperature; a sample of the stripped crude reaction product was removed for GC analysis. The GC results showed about 89.7% EtLTMPK, 0.09% ethyl levulinate and 0.52% 1,1,1-trimethylolpropane.

A 1 liter round bottom flask was charged with 401.90 g of the stripped crude reaction product and the flask placed on a rotary evaporator with a bump flask inserted between the 1 liter flask and the condenser column of the rotary evaporator. The flask and bump flask were rotated in an oil bath set to 180° C. while a vacuum of about 4-8 torr was applied. A clear liquid was observed to collect in the bump flask and periodically the vacuum on the rotary evaporator was released in order to empty the contents of the bump flask into a clean, dry storage vessel. In this way the entire batch of crude stripped reaction product was distilled and combined.

The total yield of distilled, combined EtLTMPK was 69.9 mol % based on theoretical. A sample of the distilled, combined EtLTMPK was subjected to GC and TGA analysis. The GC showed 96.8% EtLTMPK, 0.3% ethyl levulinate, and 1.8% 1,1,1-trimethylolpropane at about 1.8%. The TGA showed that EtLTMPK vaporized over the range 200°-240° C.

Example 2

Polyester of EtLTMPK and 1,3 Propane Diol

A 500 ml, 4-neck round bottom flask was oven dried at 120° C. for about 30 minutes. To the dry flask was added 235 g (0.903 mol) of the reaction product of Example 1, EtLTMPK, and 7.6 g (0.1 mol) of 1,3-propanediol (obtained from the Sigma-Aldrich Company of St. Louis, Mo.). The flask was equipped with a stir bar, thermocouple, nitrogen inlet, and Dean Stark trap with a condenser and vacuum/nitrogen outlet port. The inlet was closed and with stirring, a vacuum was applied via the outlet until the pressure reached about 15 torr. While under vacuum, the flask was heated to 100° C. with a heating mantle. The temperature and pressure were maintained until the contents of the reaction flask were observed to stop bubbling. At this point the vacuum was released by applying nitrogen to the flask, and nitrogen was then continuously applied in a slow flow through the inlet and out of the outlet. The flask was briefly opened and 51 μl (200 ppm) of titanium isoproproxide (obtained from Acros Organics of Geel, Belgium) was added via metered pipette. The temperature in the flask was increased slowly to 200° C. As the reaction progressed, liquid was observed to collect in the Dean Stark trap. At about 1,560 minutes the evolution of liquid into the trap had ceased and the temperature was increased to 210° C. Additional liquid was then observed to collect in the Dean Stark trap. At approximately 1,800 minutes liquid evolution was again observed to stop. The rate of nitrogen flow was increased and additional liquid was observed to collect in the Dean Stark trap. At 1,980 minutes the heating mantle was removed and the contents of the reaction flask allowed to cool to room temperature.

The contents of the reaction flask were analyzed for hydroxyl number, glass transition temperature, GPC molecular weight, and Brookfield viscosity. The theoretical hydroxyl number was 56; measured value was 62.7. The glass transition temperature, as measured by DSC, was 7.6° C. GPC analysis revealed number average molecular weight of 2,213 g/mol and weight average molecular weight of 5,553 g/mol, for a polydispersity of 2.50. Brookfield viscosity was measured to be 7,000 cP at 80° C.

Example 3

Homopolyester EtLTMPK

A 250 ml 3 neck round bottom flask was charged with 48.1 g (0.185 mol) of EtLTMPK from Example 1, and 4.8 μl (100 ppm) of titanium tetrabutoxide (obtained from Sigma Aldrich of St. Louis, Mo.). The flask was equipped with a Dean Stark trap with condenser and nitrogen inlet/outlet, mechanical stirrer, and nitrogen inlet. The flask was placed in an oil bath which had been heated to 60° C. and vacuum was applied with stirring until the pressure reached 0.5 torr. Nitrogen was then swept through the flask, from the inlet to the inlet/outlet. The vacuum/nitrogen degassing was repeated twice more. At the end of the three degassing steps, the vacuum was released and a sweep of nitrogen applied from the inlet through the inlet/outlet. The oil bath was then heated to 200° C. and was maintained at that temperature, while stirring the flask, for 14 hours. At this point pressure in the flask was reduced to 4.8 ton and over the ensuing 7 hours the pressure was slowly reduced from 4.8 torr to 0.4 torr. The temperature in the oil bath was then increased to 220° C. and over the ensuing 65 hours the pressure in the flask was observed to decrease from 0.4 torr to about 0.25 torr. The temperature in the flask was then increased to 240° C. and this temperature was maintained for the next 29 hours. At this point the vacuum was released in the flask and the contents of the reaction flask allowed to cool to room temperature.

A sample of the contents of the reaction flask was removed for GPC analysis. The GPC showed that the weight average molecular weight ($M_w$) was 43,474 g/mol. The number average molecular weight ($M_n$) was 6,329 g/mol for a polydispersity index of 6.7.

Example 4

Terephthalate Polyester of EtLTMPK

A 1 liter 3-neck round bottom flask was charged with 97.73 g (0.41 mol) of EtLTMPK, 78.85 g (0.41 mol) of dimethyl terephthalate (DMT; obtained from Sigma-Aldrich of St. Louis, Mo.) and 73.78 g (0.82 mol) of 1,4-butanediol (obtained from Sigma-Aldrich). The flask was equipped with a Dean Stark trap with condenser and nitrogen inlet/outlet at the top of the condenser, a mechanical stirrer, a nitrogen inlet. The contents of the flask were degassed at room temperature with 5 nitrogen/vacuum cycles. At the end of the degassing cycles the vacuum was released and nitrogen was swept from the nitrogen inlet through the inlet/outlet. The flask was then immersed in an oil bath that was initially at ambient temperature, and the temperature of the oil bath was set to 200° C. When the oil bath temperature was observed to reach 155° C. the DMT, which is a solid at ambient temperature, was observed to melt and a homogeneous mixture was formed.

Using a metered micro pipette, 35 µl of titanium tetrabutoxide (139 ppm) was injected into the homogeneous mixture in the reaction flask. Nitrogen sweep and stirring was maintained in the flask while the oil bath was held at 200° C. for 17 hours. Then a vacuum was applied to the flask such that the pressure in the flask reached between 30 and 40 torr; the vacuum was maintained for another 4 hours. Then the vacuum was increased such that the pressure in the flask reached between 2 and 10 torr and this pressure was maintained for another 4 hours. Then the temperature of the oil bath was ramped to 220° C. at 4° C./hour and this temperature was maintained for the next 62 hours. At this point a high vacuum was applied such that the pressure in the flask reached approximately 1 torr and this was maintained for the next 24 hours while the temperature in the oil bath was maintained at 220° C.

The contents of the reaction flask were observed to reach a very high viscosity, rendering stirring of the contents impracticable. Heat was removed and the contents of the reaction flask were allowed to reach room temperature. The vacuum was released and a sample of the contents of the reaction flask was removed for GPC analysis. The sample was not 100% soluble in either THF or chloroform, so only the soluble portion of the sample was analyzed. The soluble portion gave weight average molecular weight ($M_w$) 35,082 and number average molecular weight ($M_n$) 2,468 for a polydispersity of 14.2.

Example 5

Trimethylolethane Ketal of Ethyl Levulinate (EtLTMEK)

A 1 liter, single-neck round bottom flask was charged with 450.88 g (3.13 mol) of ethyl levulinate, 188.62 g (1.57 mol) of 1,1,1-trihydroxymethylethane, and 8.40 (0.158 mmol) of concentrated sulfuric acid. The flask was attached to a rotary evaporator with an oil bath set to 75° C. and a vacuum of approximately 7 torr. The flask was rotated on the rotary evaporator for the next 1.5 hours. A small amount of liquid was observed to collect in the receiving flask. The temperature in the oil bath was increased to 90° C. and this temperature was maintained for the following 1 hour and 15 minutes. Additional liquid was observed to collect in the collection flask. The temperature of the oil bath was then increased to 100° C. and was maintained at that temperature for 2 hours and 45 minutes, during which time additional liquid was observe to collect in the collection flask. The vacuum was released and the flask was removed from the rotary evaporator and the contents allowed to reach room temperature. A sample was then removed for GC analysis. The GC showed that the contents of the reaction flask contained approximately 58.0% of the trimethylolethane ketal of ethyl levulinate (EtLTMEK), 35.2% ethyl levulinate and 1.2% 1,1,1-trimethylolethane.

Teflon boiling chips and a stir bar were added to the flask and a fractionation column, condenser, and catch flask were attached to the flask. A vacuum was applied until the pressure in the flask reached 5.5 torn A heating mantle was then added to the flask and turned on to a setting of 7 out of 10. When the head temperature was observed to reach about 88° C. a liquid was observed to distill into the catch flask. After the evolution of the liquid had stopped the head temperature was observed to go up to about 164° C. and another liquid was observed to start collecting in the flask. A small amount of this liquid was collected and then the heating mantle was removed from the flask and the contents of the flask allowed to reach room temperature. The vacuum was then released. A sample of the contents of the flask was removed for GC analysis. The GC trace showed approximately 89% of EtLTMEK, 0.14% ethyl levulinate, and 0.37% 1,1,1-trimethylolethane.

The contents of the reaction flask were transferred to a fresh 1 liter single neck round bottom flask, which was placed onto a rotary evaporator with a 500 ml bump flask. The flask was rotated on the rotary evaporator with an oil bath temperature of 167° C. and a vacuum of approximately 7 torr. Over the next 40 minutes the temperature of the oil bath was increased to 180° C. and this temperature was maintained for about 2 hours while a liquid was observed to distill into the bump flask. As distillation progressed the bump flask filled up with the liquid which was periodically emptied by releasing the vacuum and emptying the bump flask into a clean vessel. When the distillation was complete, the combined distilled fractions were subjected to GC. The GC showed that the contents of the distilled combined fractions were approximately 95.6% EtLTHEK, 0.5% ethyl levulinate, and 1.6% 1,1,1-trimethylolethane. The combined fractions gave a total yield, based on calculated theoretical yield, of 69.5 mol %.

Example 6

Polyester homopolymer of EtLTMEK

A 1 liter, pear shaped single-neck round bottom flask was charged with 51.0 g of EtLTMEK (0.207 mol) and 0.23 g (1125.5 ppm) sodium methoxide (delivered as a 25 weight % solution in methanol, obtained from the Sigma-Aldrich Company of St. Louis, Mo.). A 250 ml bump flask was attached to the reaction flask and the reaction flask and bump flask applied to a rotary evaporator. The flask was rotated on the rotary evaporator for 50 minutes with an oil bath temperature of 120° C. and a vacuum of 7-8 torr. The temperature of the oil bath was then increased to 140° C. and this temperature was maintained for the next 70 minutes. The temperature of the oil bath was then increased to 180° C. and this temperature was maintained for about 5.5 hours. Then the temperature of the oil bath was increased to 200° C. and a vacuum of between 250 and 500 millitorr was applied to the flask. This temperature and pressure were maintained for approximately 5 hours. The temperature of the oil bath was then increased to 220° C. and this temperature was maintained for 33 hours. The vacuum was released and the flask was removed from the rotary evaporator and allowed to reach room temperature.

In order to remove the contents of the reaction flask the flask was warmed sufficiently to provide flow sufficient to pour the contents. The contents of the reaction flask were then subjected to GPC which showed a weight average molecular weight ($M_w$) of 45,046 g/mol and number average molecular weight ($M_n$) 10,096 g/mol, for a polydispersity of 4.46. DSC analysis showed that the glass transition temperature ($T_g$) of the polymer was 40° C.

Example 7

Reactive Isocyanate Prepolymer of Polyester of Example 2

A 250 ml, 3-neck round bottom flask was charged with 200.0 g of the reaction product of Example 2. The flask was equipped with a magnetic stir bar, a nitrogen inlet, a nitrogen outlet, and a thermocouple. The flask was placed in a heating mantle and heated to 80° C. Nitrogen was blown in through the inlet and out of the outlet while the temperature was maintained with stirring for approximately 16 hours to result in the dried product of Example 2. A 500 ml resin kettle was charged with 60.9 g (0.24 mol) of methylene diphenyl-4,4'-diisocyanate (MDI). The resin kettle was then clamped to its lid, which was equipped with a mechanical stirrer, nitrogen inlet, nitrogen outlet, and a thermocouple. Nitrogen was flowed through the inlet and out of the outlet, with stirring, while the flask was heated to 80° C. using a heating mantle. To the flask was added 167.1 g (0.09 mol) of the dried polyol of Example 2. The heat and stirring were maintained for 3 hours, after which isocyanate value was measured by removing a sample from the resin kettle. The isocyanate number was measured to be 3.8 weight percent. The theoretical value was 6.6 weight percent.

Example 8

Polyurethane of the Reactive Urethane of Example 7

A 250 ml, 3-neck roundbottom flask was charged with an undetermined amount of 1,3-propanediol (obtained from Sigma-Aldrich Chemicals of St. Louis, Mo.). The flask was equipped with nitrogen inlet, nitrogen outlet, thermocouple, and a magnetic stir bar, and heating with stirring and nitrogen flow for approximately 16 hours at 80° C., to provide dried 1,3-propanediol. A 20.0 g aliquot of the dried 1,3-propanediol were removed from the drying flask and placed in a beaker along with 5 µl of dibutyltin dilaurate (Air Products Company). The diol and tin catalyst were mixed briefly by hand, and then 6.7 g of the mixture was added to the resin flask containing the reaction product of Example 7, which had been preheated to 80° C. under nitrogen flow. The mixture of was stirred for approximately 2 minutes.

The contents of the resin flask were partially emptied into a custom made Teflon mold measuring 25.4 cm×25.4 cm×0.5 mm. The mold was preheated in an oven to 110° C. After filling the mold with the mixture from the resin flask, the mold was covered with Teflon coated aluminum foil (BYTAC®, obtained from Fisher Scientific of Waltham, Mass.). A second sheet of Teflon coated aluminum foil was placed under the mold. A 0.1524 cm thick steel plate was placed on top and a second plate placed beneath the Teflon covered aluminum foil, to form a compression molding "sandwich". The sandwich was placed in a Carver Model 4122 pneumatic heated platen press (obtained from Carver, Inc. of Wabash, Ind.) of that was preheated to 105° C. The press was closed and pressure of 5,000 lbs applied to the sandwich. The heat and pressure were maintained for 1 hour. The mold was then removed from the press and placed in an oven at 110° C. for 24 hours. The sample was removed from the oven and a solid, flexible molded sheet comprising the material from the resin flask was removed from the mold.

A second compression molding sandwich was formed by layering the molded sheet on its two major sides Teflon coated aluminum foil sheets and steel plates. The second sandwich was placed in the press that was preheated to 188° C. The platens of the press were closed so as to contact the sandwich but without adding measurable pressure. This position was maintained for approximately 3 minutes in order to preheat the sandwich. The pressure was then increased to 5,000 lbs. and this was maintained for 5 minutes. The sandwich was removed from the press and allowed to cool for approximately 1 minute before removing a pressed film from the sandwich.

The pressed film was measured to be 1.52 mm thick, was uniform and without bubbles, was transparent, and had a very slight yellow color. The pressed film was characterized by DMA and DSC. The DMA showed that the peak of the tan Δ was at 87.3° C. DSC showed that the $T_g$ was 51.4° C. with a broad melting range between about 190° C. and 210° C.

Example 9

MDI Polyurethane of the Polyester of Example 2

A 20 ml scintillation vial was charged with 6.6 g of the reaction product of Example 2, which had been preheated to 110° C. in order to provide sufficient flow to be pourable. Methylene diphenyl-4,4'-diisocyanate (MDI, 0.95 g) was added to the scintillation vial and 1 µl dibutyltin dilaurate was added to the vial via microliter syringe. The scintillation vial was heated with a heat gun until the MDI was observed to melt. The contents of the scintillation vial were stirred with a wooden tongue depressor. The stirred mixture was capped and placed in an oven set to 100° C. for approximately 2 hours. The sample was then allowed to cool to room temperature and was removed from the vial by breaking the vial. Glass transition temperature ($T_g$) was measured by DSC and determined to be 41.37° C.

Example 10

Ethyl Acetoacetate Glycerol Ketal ("EtAGK")

A 500 mL 3-neck round bottom flask was charged with 186.08 g (2.00 mol) glycerol (obtained from Acros Organics of Geel, Belgium) and 1045.88 g (8.04 mol) ethyl acetoacetate (obtained from Sigma Aldrich Company of St. Louis, Mo.). The contents of the flask were observed to consist of a heterogeneous mixture of two liquid phases. The flask was equipped with an overhead mechanical stirrer, a Dean-Stark separator with an overhead condenser, and a thermocouple. The contents of the flask were blanketed with a nitrogen stream and heated to 110° C. while stirring. Once the contents were at 90° C., 21.3 µL ($2.0 \times 10^{-4}$ moles) of concentrated sulfuric acid (obtained from the Sigma Aldrich Company of St. Louis, Mo.) was added into the flask below the surface of the contents by pipette. The contents of the flask began to bubble. The initial pressure in the flask was set to 300 Torr, and pressure was then ramped from 300 Torr to about 30 Torr over about 7 min. The contents of the flask were stirred for an additional 60 min at 25-30 Torr. During this time, a distillate was collected in the Dean Stark separator. The distillate was observed to separate as it cooled. A sample of the reaction mixture was removed for GC-MS analysis. The GC trace showed no evidence of glycerol. Only excess ethyl acetoacetate and the ethyl acetoacetate-glycerol ketal (EtAGK) were observed.

The EtAGK reaction product was poured into a beaker and neutralized by adding about 109 g (10 wgt %) of basic alumina (from Sigma Aldrich) and stirring the mixture for about 30 minutes at room temperature. The solids were filtered from the mixture using a fritted glass filter, fine grade. The liquids were vacuum distilled at between about 35 and 67 Ton using a 1 liter flask, fractionation column, condenser, and a cow with 3 catch flasks. A first liquid was observed to distil at about 95° C., and this was collected and analyzed by GC-MS and determined to be 100% ethyl acetoacetate. A second liquid was observed to distil at about 165° C. A very small amount of residual material was left in the distillation flask at the end of the distillation. In the catch flask for the second liquid, both liquid and an appreciable amount of a crystalline solid were observed. GC-MS showed that the second liquid was 99% EtAGK.

Example 11

Homopolyester of EtAGK

A 250 ml 3 neck round bottom flask was charged with 238.1 g (1.17 mol) of the product of Example 10, and 11.56 g (0.01 mol) of 1,6-hexane diol (obtained from Acros Organics of Geel, Belgium). The flask was equipped with a thermocouple, stir bar, nitrogen inlet, and Dean Stark trap with condenser and nitrogen outlet. The flask was heated to 120° C. and 2 vacuum/nitrogen degassing cycles were carried out at elevated temperature. The flask was backfilled with nitrogen after degassing, and 150 µl (600 ppm) of titanium tetrabutoxide were added to the reaction flask via metered microliter pipette. With stirring and nitrogen sweep continued, the temperature of the contents of the flask was increased to 235° C. The temperature was maintained for approximately 4 hours, during which time liquid was observed to collect in the Dean Stark trap. At the end of 4 hours the condensation of liquid was observed to stop and the heat source was removed from the flask.

Upon reaching ambient temperature the reaction mixture was highly viscous and dark brown to black in color. Hydroxyl number was measured to be 25 with a theoretical value of 56. DSC was used to measure the glass transition temperature of the mixture which was −17.6° C. GPC was used to determine that the number average molecular weight ($M_n$) was 1,776 g/mol.

Example 12

Reactive Isocyanate Prepolymer of Polyester of Example 11

Using the procedure of Example 7, 136.5 g of the reaction product of Example 11 was reacted with 47.4 g of methylene diphenyl-4,4'-diisocyanate (MDI) to give an isocyanate prepolymer with an isocyanate number measured to be 3.95; theoretical was 6.2%.

The isocyanate prepolymer was then reacted with 1,3-propane diol and dibutyltin dilaurate according to the procedure of Example 8. The amount of 1,3-propane diol used was 6.15 g and the amount of dibutyltin dilaurate was 2.16 µl. The resulting polyurethane reaction product was compression molded, cured in the oven, and pressed between sheets in the same manner as in Example 8. DSC was used to measure the glass transition temperature ($T_g$) of the resulting pressed sheet; $T_g$ was measured to be 37.8° C.

Example 13

Homopolymerization of the Ketal Reaction Product of Ethyl Pyruvate and Glycerol

A 1 liter, 3-neck round bottom flask was charged with 306.5 g (2.64 mol) of ethyl pyruvate (obtained from Sigma-Aldrich Company of St. Louis, Mo.) and 121.6 g (1.32 mol) of glycerol (obtained from Cargill, Inc. of Wayzata, Minn.) and 214 g of toluene. The flask was equipped with a mechanical stirrer, a Dean Stark trap with condenser, and a thermocouple. Using a heating mantle, the flask was heated to 110° C. with stirring. Upon reaching 110° C. the flask was briefly opened and 12.56 µl ($2.35 \times 10^{-4}$ mol) of concentrated sulfuric acid was injected with a metered micropipette. Heat and stirring were continued for approximately 2 hours 40 minutes. The contents of the flask were then allowed to cool to ambient temperature.

Approximately 100 ml of the contents of the reaction flask were removed and placed in a separatory funnel. An approximately equal volume of a saturated solution of sodium bicarbonate was added to the separatory funnel and the mixture was shaken to wash the contents of the flask. The organic layer collected and washed with an approximately equal volume of a concentrated sodium chloride solution. The organic layer was collected and dried over sodium sulfate. The sodium sulfate was filtered away from the organic layer, and the organic layer was added to a 1 liter round bottom flask and placed on a rotary evaporator with a bump flask. Toluene was removed at a bath temperature of 50° C. and then the bath temperature was increased to 90° C. and ethyl pyruvate was stripped. The total time on the rotary evaporator was about 1 hour 35 minutes. A sample of the contents of the flask was removed for analysis. GC-MS showed about 99.6% conversion based on the disappearance of glycerol.

A 250 ml round bottom flask was charged with 30.26 g of the ketal reaction product and 0.129 g (1,000 ppm) of sodium methoxide (25 wt %, obtained from Sigma-Aldrich Company of St. Louis, Mo.) in methanol. The flask was placed on a rotary evaporator with a 250 ml bump flask and a bath temperature of 100° C. A vacuum of approximately 15 torr was applied to the rotary evaporator. Over the course of the next 1 hour, 15 minutes, the vacuum was decreased to about 9-10 torr and the temperature in the oil bath was increased to about 150° C. After a total of 14.5 additional hours the contents of the flask were removed from the rotary evaporator and allowed to cool to room temperature. A sample was removed for GPC analysis, which showed $M_n$ of 810, $M_w$ of 1044, for a polydispersity of 1.29.

A number of embodiments of the disclosure have been described. Nevertheless, it will be understood that various modifications may be made without departing from the spirit and scope of the disclosure. The various embodiments described above are provided by way of illustration only and should not be construed to limit the claims attached hereto. The present invention may suitably comprise, consist of, or consist essentially of, any of the disclosed or recited elements. Thus, the invention illustratively disclosed herein can be suitably practiced in the absence of any element which is not specifically disclosed herein. Various modifications and changes will be recognized that may be made without following the example embodiments and applications illustrated and described herein, and without departing from the true spirit and scope of the following claims.

We claim:

1. A polyester having a structure corresponding to (1):

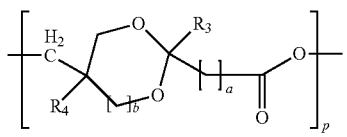

(1)

wherein
the polyester is derived from

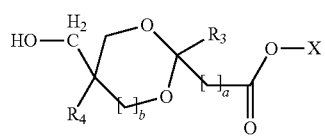

(1a)

wherein in formulas (1) and (1a),
p is an integer of at least 2,
a is 0 or 1,
b is 0 or 1,
$R_3$ is methyl;
$R_4$ is hydrogen, methyl, or ethyl, and
X is hydrogen or a lower alkyl.

2. The polyester of claim 1 wherein p is 10 or greater.
3. The polyester of claim 1 wherein p is 100 or greater.
4. A material comprising a compound having a structure corresponding structures (2), (3), or a mixture thereof:

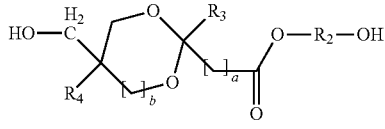

(2)

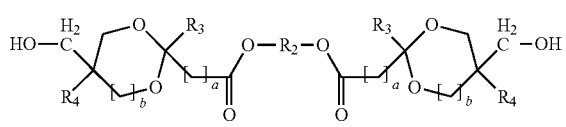

(3)

wherein
a equals 0 or 1;
b equals 0 or 1;
$R_2$ represents an alkylene, cycloalkylene or aralkylene group of 2-36 carbons, with the hydroxyl groups attached to saturated carbons, and optionally comprises halogen, ether, ester, carbonate, amide or urethane groups;
$R_3$ is methyl; and
$R_4$ is hydrogen, methyl, or ethyl.

5. The material of claim 4 wherein $R_2$ is a residue of diethylene glycol or 1,6-hexanediol.
6. A polyurethane comprising the reaction product of one or more material of claim 4 and one or more organic diisocyanates.
7. A polyhydroxy compound having a structure corresponding to (4):

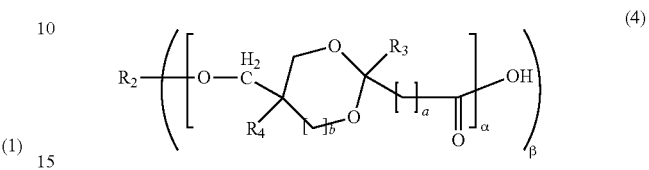

(4)

wherein
a equals 0 or 1;
b equals 0 or 1;
$R_2$ represents an alkylene, cycloalkylene or aralkylene group of 2-36 carbons, with the hydroxyl groups attached to saturated carbons, and may contain halogen, ether, ester, carbonate, amide or urethane groups;
$R_3$ is methyl;
$R_4$ is hydrogen, methyl, or ethyl;
$\alpha$ is an integer of about 1 to 100; and
$\beta$ is an integer of at least 2.

8. The polyhydroxy compound of claim 7 having an average hydroxyl equivalent weight of between about 200 and 5000.
9. The polyhydroxy compound of claim 7 wherein $\beta$ is between 2 and 10.
10. A polyurethane comprising the reaction product of one or more polyhydroxy compounds of claim 7 and one or more organic diisocyanates.
11. An isocyanate prepolymer having a structure corresponding to (5):

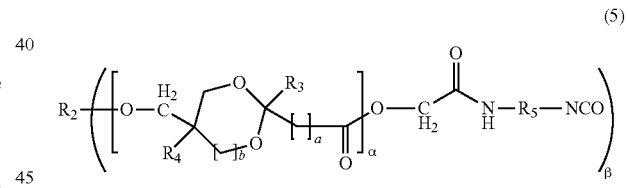

(5)

wherein
a equals 0 or 1;
b equals 0 or 1;
$R_2$ represents an alkylene, cycloalkylene or aralkylene group of 2-36 carbons, with the hydroxyl groups attached to saturated carbons, and may contain halogen, ether, ester, carbonate, amide or urethane groups;
$R_3$ is methyl;
$R_4$ is hydrogen, methyl, or ethyl;
$R_5$ is the residue of an organic diisocyanate having a molecular weight of about 100 to 1,000 g/mol;
$\alpha$ is an integer of about 1 to 100; and
$\beta$ is an integer of at least 2.

12. The isocyanate prepolymer of claim 11 wherein $R_5$ is the residue of an organic diisocyanate having a molecular weight of about 140 to 400 g/mol.
13. The isocyanate prepolymer of claim 11 wherein $\beta$ is between 2 and 10.
14. A polyurethane comprising the reaction product of one or more isocyanate prepolymers of claim 11 and one or more polyols.

15. A copolyester having a structure corresponding to (6)):

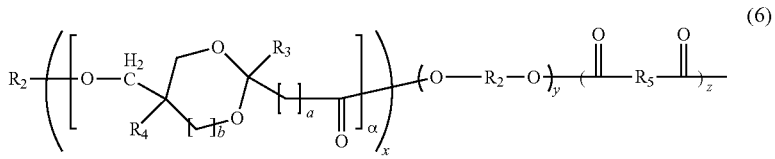

wherein
a equals 0 or 1;
b equals 0 or 1;
$R_2$ represents an alkylene, cycloalkylene or aralkylene group of 2-36 carbons, with the hydroxyl groups attached to saturated carbons, and may contain halogen, ether, ester, carbonate, amide or urethane groups;
$R_3$ is methyl;
$R_4$ is hydrogen, methyl, or ethyl;
$R_5$ is the residue of an organic diacid having a molecular weight of about 100 to 1,000 g/mol;
α is an integer of about 1 to 100; and
x, y and z represent molar fractions of the indicated residue in the copolymer, such that the sum of (x+y+z) equals 1.

16. The copolyester of claim 15 wherein $R_5$ is the residue of an organic diacid having a molecular weight of about 120 to 400 g/mol.

17. The copolyester of claim 15 comprising two or more hydroxyl endgroups.

18. A polyurethane comprising the reaction product of one or more copolyesters of claim 17 and one or more organic diisocyanates.

19. A polyester having a structure corresponding to (7):

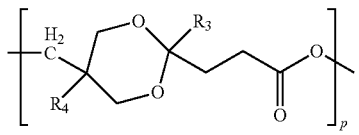

wherein
the polyester is derived from

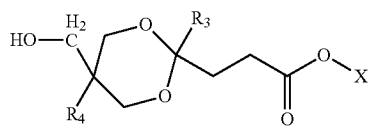

wherein in formulas (7) and (7a),
p is an integer of at least 2,
$R_3$ is methyl;
$R_4$ is hydrogen, methyl, or ethyl, and
X is hydrogen or a lower alkyl.

20. The compound of claim 19 wherein p is 10 or greater.

21. The compound of claim 19 wherein p is 100 or greater.

22. A material comprising a compound having a structure corresponding structures (8), (9), or a mixture thereof:

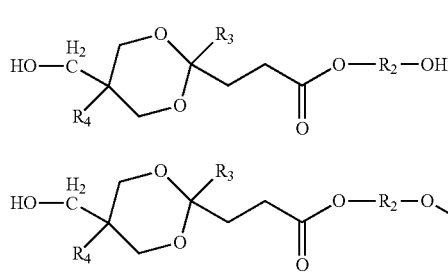

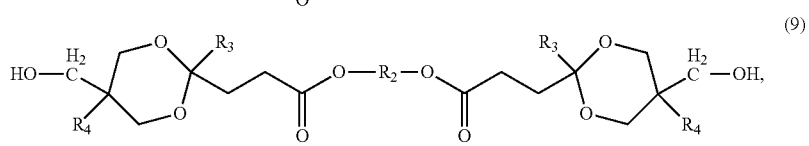

wherein
$R_2$ represents an alkylene, cycloalkylene or aralkylene group of 2-36 carbons, with the hydroxyl groups attached to saturated carbons, and may contain halogen, ether, ester, carbonate, amide or urethane groups;
$R_3$ is methyl; and
$R_4$ is hydrogen, methyl, or ethyl.

23. The material of claim 22 wherein $R_2$ is a residue of diethylene glycol or 1,6-hexanediol.

24. A polyurethane comprising the reaction product of one or more of the compounds of claim 22 and one or more organic diisocyanates.

25. A polyhydroxy compound having a structure corresponding to (10):

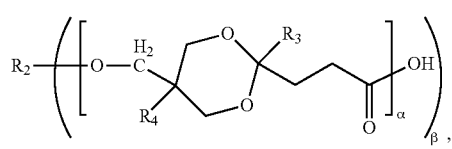

wherein
$R_2$ represents an alkylene, cycloalkylene or aralkylene group of 2-36 carbons, with the hydroxyl groups attached to saturated carbons, and may contain halogen, ether, ester, carbonate, amide or urethane groups;
$R_3$ is methyl;
$R_4$ is hydrogen, methyl, or ethyl;
α is an integer of about 1 to 100; and
β is an integer of at least 2.

26. The polyhydroxy compound of claim 25 having an average hydroxyl equivalent weight of between about 200 and 5000.

27. The polyhydroxy compound of claim 25 wherein β is between 2 and 10.

28. A polyurethane comprising the reaction product of one or more polyhydroxy compounds of claim 25 and one or more organic diisocyanates.

29. An isocyanate prepolymer having a structure corresponding to (11):

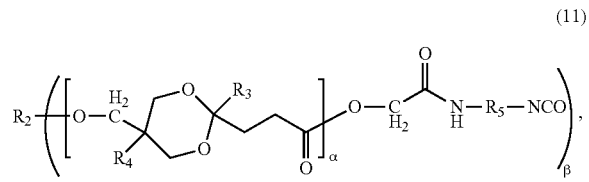

wherein
R₂ represents an alkylene, cycloalkylene or aralkylene group of 2-36 carbons, with the hydroxyl groups attached to saturated carbons, and may contain halogen, ether, ester, carbonate, amide or urethane groups;
R₃ is methyl;
R₄ is hydrogen, methyl, or ethyl;
R₅ is the residue of an organic diisocyanate having a molecular weight of about 100 to 1,000 g/mol;
α is an integer of about 1to 100; and
β is an integer of at least 2.

30. The isocyanate prepolymer of claim 29 wherein R₅ is the residue of an organic diisocyanate having a molecular weight of about 140 to 400 g/mol.

31. The isocyanate prepolymer of claim 29 wherein β is between 2 and 10.

32. A polyurethane comprising the reaction product of one or more isocyanate prepolymers of claim 29 and one or more polyols.

33. A copolyester having a structure corresponding to (12):

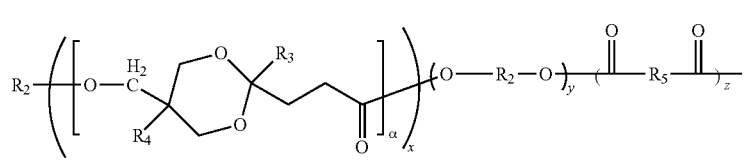

wherein
R₂ represents an alkylene, cycloalkylene or aralkylene group of 2-36 carbons, with the hydroxyl groups attached to saturated carbons, and may contain halogen, ether, ester, carbonate, amide or urethane groups;
R₃ is methyl;
R₄ is hydrogen, methyl, or ethyl;
R₅ is the residue of an organic diacid having a molecular weight of about 100 to 1,000 g/mol;
α is an integer of about 1to 100; and
x, y and z represent molar fractions of the indicated residue in the copolymer, such that the sum of (x+y+z) equals 1.

34. The copolyester of claim 33 wherein R₅ is the residue of an organic diacid having a molecular weight of about 120 to 400 g/mol.

35. The copolyester of claim 33 comprising two or more hydroxyl endgroups.

36. A polyurethane comprising the reaction product of one or more copolyesters of claim 35 and one or more organic diisocyanates.

37. The polyurethane of claim 6, wherein the diisocyanate is at least one selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethylcyclopentane, 1-isocyanato-3-isocyanatomethyl-3,5,5-trimethyl-cyclohexane, bis-(4-isocyanatocyclohexyl)methane, 2,4'-dicyclohexylmethane diisocyanate, 4,4'-dicyclohexylmethane diisocyanate, 1,3-bis-(isocyanatomethyl)cyclohexane, 1,4-bis-(isocyanatomethyl)cyclohexane,bis-(4-isocyanato-3-methyl-cyclohexyl)methane, α,α,α',α'-tetramethyl-1,3-xylylene diisocyanate, α,α,α',α'-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, and 1,5-diisocyanato naphthalene.

38. The polyurethane of claim 10, wherein the diisocyanate is at least one selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethylcyclopentane, 1-isocyanato-3-isocyanatomethyl-3,5,5-trimethyl-cyclohexane, bis-(4-isocyanatocyclohexyl)methane, 2,4'-dicyclohexylmethane diisocyanate, 4,4'-dicyclohexylmethane diisocyanate, 1,3-bis-(isocyanatomethyl)cyclohexane, 1,4-bis-(isocyanatomethyl)cyclohexane, bis-(4-isocyanato-3-methyl-cyclohexyl)methane, α,α,α',α'-tetramethyl-1,3-xylylene diisocyanate, α,α,α',α'-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, and 1,5-diisocyanato naphthalene.

39. The polyurethane of claim 11, wherein the diisocyanate is at least one selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate, 1-isocyanato-2-isocyanatomethylcyclopentane, 1-isocyanato-3 -isocyanatomethyl-3,5,5-trimethyl-cyclohexane, bis-(4-isocyanatocyclohexyl)methane, 2,4'-dicyclohexylmethane diisocyanate,4,4'-dicyclohexylmethane diisocyanate,1,3-bis-(isocyanatomethyl)cyclohexane, 1,4-bis-(isocyanatomethyl)cyclohexane, bis-(4-isocyanato-3-methyl-cyclohexyl)methane, α,α,α',α'-tetramethyl-1,3-xylylene diisocyanate, α,α,α',α'-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, and 1,5-diisocyanato naphthalene.

40. The polyurethane of claim 18, wherein the diisocyanate is at least one selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate,1-isocyanato-2-isocyanatomethylcyclopentane, 1-isocyanato-3-isocyanatomethyl-3,5,5-trimethyl-cyclohexane, bis-(4-isocyanatocyclohexyl)methane, 2,4'-dicyclohexylmethane diisocyanate, 4,4'-dicyclohexylmethane diisocyanate, 1,3-bis-(isocyanatomethyl)cyclohexane, 1,4-bis-(isocyanatomethyl)cyclohexane, bis-(4-isocyanato-3-methyl-cyclohexyl)methane, $\alpha,\alpha,\alpha',\alpha'$-tetramethyl-1,3-xylylene diisocyanate, $\alpha,\alpha,\alpha',\alpha'$-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, and 1,5-diisocyanato naphthalene.

41. The polyurethane of claim 24, wherein the diisocyanate is at least one selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate,1-isocyanato-2-isocyanatomethylcyclopentane, 1-isocyanato-3-isocyanatomethyl-3,5,5-trimethyl-cyclohexane, bis-(4-isocyanatocyclohexyl)methane, 2,4'-dicyclohexylmethane diisocyanate, 4,4'-dicyclohexylmethane diisocyanate, 1,3-bis-(isocyanatomethyl)cyclohexane, 1,4-bis-(isocyanatomethyl)cyclohexane, bis-(4-isocyanato-3-methyl-cyclohexyl)methane, $\alpha,\alpha,\alpha',\alpha'$-tetramethyl-1,3-xylylene diisocyanate, $\alpha,\alpha,\alpha',\alpha'$-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, and 1,5-diisocyanato naphthalene.

42. The polyurethane of claim 28, wherein the diisocyanate is at least one selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate,1-isocyanato-2-isocyanatomethylcyclopentane, 1-isocyanato-3-isocyanatomethyl-3,5,5-trimethyl-cyclohexane, bis-(4-isocyanatocyclohexyl)methane, 2,4'-dicyclohexylmethane diisocyanate, 4,4'-dicyclohexylmethane diisocyanate, 1,3-bis-(isocyanatomethyl)cyclohexane, 1,4-bis-(isocyanatomethyl)cyclohexane, bis-(4-isocyanato-3-methyl-cyclohexyl)methane, $\alpha,\alpha,\alpha',\alpha'$-tetramethyl-1,3-xylylene diisocyanate, $\alpha,\alpha,\alpha',\alpha'$-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, and 1,5-diisocyanato naphthalene.

43. The polyurethane of claim 29, wherein the diisocyanate is at least one selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate,1-isocyanato-2-isocyanatomethylcyclopentane, 1-isocyanato-3-isocyanatomethyl-3,5,5-trimethyl-cyclohexane, bis-(4-isocyanatocyclohexyl)methane, 2,4'-dicyclohexylmethane diisocyanate, 4,4'-dicyclohexylmethane diisocyanate, 1,3-bis-(isocyanatomethyl)cyclohexane, 1,4-bis-(isocyanatomethyl)cyclohexane, bis-(4-isocyanato-3-methyl-cyclohexyl)methane, $\alpha,\alpha,\alpha',\alpha'$-tetramethyl-1,3-xylylene diisocyanate, $\alpha,\alpha,\alpha',\alpha'$-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, and 1,5-diisocyanato naphthalene.

44. The polyurethane of claim 36, wherein the diisocyanate is at least one selected from 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3-diisocyanate, cyclohexane-1,4-diisocyanate,1-isocyanato-2-isocyanatomethylcyclopentane, 1-isocyanato-3-isocyanatomethyl-3,5,5-trimethyl-cyclohexane, bis-(4-isocyanatocyclohexyl)methane, 2,4'-dicyclohexylmethane diisocyanate, 4,4'-dicyclohexylmethane diisocyanate, 1,3-bis-(isocyanatomethyl)cyclohexane, 1,4-bis-(isocyanatomethyl)cyclohexane, bis-(4-isocyanato-3-methyl-cyclohexyl)methane, $\alpha,\alpha,\alpha',\alpha'$-tetramethyl-1,3-xylylene diisocyanate, $\alpha,\alpha,\alpha',\alpha'$-tetramethyl-1,4-xylylene diisocyanate, 1-isocyanato-1-methyl-4(3)-isocyanatomethyl cyclohexane, 2,4-hexahydrotolylene diisocyanate, 2,6-hexahydrotolylene diisocyanate, 1,3-phenylene diisocyanate, 1,4-phenylene diisocyanate, 2,4-tolylene diisocyanate, 2,6-tolylene diisocyanate, 2,2'-diphenylmethane diisocyanate, 2,4'-diphenylmethane diisocyanate, 4,4'-diphenylmethane diisocyanate, and 1,5-diisocyanato naphthalene.

45. The copolyester of claim 15, wherein the organic diacid is at least one selected from succinic acid, glutaric acid, adipic acid, pimelic acid, suberic acid, azelaic acid, sebacic acid, nonanedicarboxylic acid, decanedicarboxylic acid, terephthalic acid, isophthalic acid, o-phthalic acid, tetrahydrophthalic acid, hexahydrophthalic acid, maleic acid, fumaric acid, naphthalene dioc acid, dimerized fatty acids, and hydrogenated dimerized fatty acid.

46. The copolyester of claim 33, wherein the organic diacid is at least one selected from succinic acid, glutaric acid, adipic acid, pimelic acid, suberic acid, azelaic acid, sebacic acid, nonanedicarboxylic acid, decanedicarboxylic acid, terephthalic acid, isophthalic acid, o-phthalic acid, tetrahydrophthalic acid, hexahydrophthalic acid, maleic acid, fumaric acid, naphthalene dioc acid, dimerized fatty acids, and hydrogenated dimerized fatty acid.

* * * * *